United States Patent [19]
Hei et al.

[11] Patent Number: 5,567,444
[45] Date of Patent: Oct. 22, 1996

[54] POTENTIATED AQUEOUS OZONE CLEANING AND SANITIZING COMPOSITION FOR REMOVAL OF A CONTAMINATING SOIL FROM A SURFACE

[75] Inventors: Robert D. Hei, Oakdale; Guange-jong J. Wei, Mendota Heights; Bruce R. Cords, Eagan; Keith D. Lokkesmoe, Savage, all of Minn.

[73] Assignee: Ecolab Inc., St. Paul, Minn.

[21] Appl. No.: 532,485

[22] Filed: Sep. 22, 1995

Related U.S. Application Data

[63] Continuation-in-part of Ser. No. 114,193, Aug. 20, 1993, Pat. No. 5,484,549.

[51] Int. Cl.$^6$ .............................. A61L 9/00; A01N 37/00; A01N 39/00; C11D 7/54
[52] U.S. Cl. ...................... 424/616; 252/174.14; 422/28; 422/29; 424/613; 514/558; 514/574; 510/234; 510/370; 510/372; 134/2; 134/22.13; 134/22.14
[58] Field of Search .................................. 424/616, 613; 422/28, 29; 514/558, 574; 252/95, 103, 156, 173, 174.14

[56] References Cited

U.S. PATENT DOCUMENTS

| | | | |
|---|---|---|---|
| 3,217,294 | 11/1965 | Gerlach et al. | 340/146.34 |
| 3,249,985 | 5/1966 | Weller et al. | 29/96 |
| 4,063,890 | 12/1977 | Baron et al. | 21/54 R |
| 4,104,187 | 8/1978 | Sibley et al. | 252/106 |
| 4,116,859 | 9/1978 | Merkl | 252/186 |
| 4,214,014 | 7/1980 | Hofer et al. | 427/40 |
| 4,505,836 | 3/1985 | Fairchild | 252/174.14 |
| 4,666,722 | 5/1987 | Creed et al. | 426/393 |
| 4,690,772 | 9/1987 | Tell et al. | 252/106 |
| 4,898,679 | 2/1990 | Siegel et al. | 210/752 |
| 4,933,411 | 6/1990 | Gifford | 426/399 |
| 4,956,098 | 9/1990 | Stevens et al. | 210/748 |
| 4,959,124 | 11/1990 | Tsai | 162/65 |
| 5,006,124 | 4/1991 | Tieckelmann et al. | 8/111 |
| 5,053,140 | 10/1991 | Hurst | 210/704 |
| 5,097,556 | 3/1992 | Engel et al. | 8/158 |
| 5,118,322 | 6/1992 | Wasinger et al. | 8/111 |
| 5,180,500 | 1/1993 | McConnell | 210/721 |
| 5,181,399 | 1/1993 | Engel et al. | 68/13 R |
| 5,192,459 | 3/1993 | Tell et al. | 252/106 |
| 5,330,672 | 7/1994 | Langer et al. | 252/108 |
| 5,330,752 | 7/1994 | Park et al. | 424/94.4 |
| 5,332,518 | 7/1994 | Kuroda et al. | 252/99 |
| 5,332,527 | 7/1994 | Heinzman et al. | 252/546 |

FOREIGN PATENT DOCUMENTS

| | | |
|---|---|---|
| 357710 | 1/1929 | Belgium . |
| 1345086 | 10/1962 | France . |
| 3007670A1 | 9/1981 | Germany . |
| 3209930 | 9/1983 | Germany . |
| 3320841A1 | 1/1985 | Germany . |
| 3917250 | 12/1990 | Germany . |
| 62-61574 | 3/1987 | Japan . |
| 64-51071 | 2/1989 | Japan . |
| 1-305956 | 12/1989 | Japan . |
| 2-172593 | 7/1990 | Japan . |
| 3-249985 | 7/1991 | Japan . |
| 3-217294 | 9/1991 | Japan . |
| 4-145997 | 5/1992 | Japan . |
| 4-188083 | 7/1992 | Japan . |

OTHER PUBLICATIONS

Environmental Aspects of the Use of Alkaline Cleaning Solutions, A. Grabhoff, Federal Dairy Research Centre, Kiel, F. R., Germany, pp. 107–114) (1989).

The Role of Hydroxyl Radical Reactions in Ozonation Processes in Aqueous Solutions, J. Hoigne and H. Bader, Swiss Fed. Inst. of Tech., Zurich Inst. for Aquatic Sciences and Water Pollution Control, Duebendorf, 8600 Switzerland, pp. 377–386 (Oct. 1975).

Industries Alimentaires et Agricoles, 1978, 95(9/10), pp. 1089–1091, Paragraph 1.2.1 Ozone (English translation attached).

"Surface Disinfection of Raw Produce", *Dairy, Food and Environmental Sanitation*, Larry R. Beuchat, vol. 12, No. 1, pp. 6–9 (Jan. 1992).

"Effect of Ozonated Water on Postharvest Pathogens of Pear in Laboratory and Packinghouse Tests", *Plant Disease*, R. A. Spotts et al., vol. 76, No. 3, pp. 256–259 (Mar., 1992).

Databasw WPI, Derwent Publications Ltd., London, GB; AN 90–027139 & JP,A,1 305 956 (Chiyoda Seisakusho, Sakara Seiki, Bodai Embody) Nov. 12, 1989.

A comparison of the Effectiveness of Ozone and Chlorine in Controlling Biofouling within Condensors Using Fresh Water as a Coolant, John F. Garey et al., Ozone: Science and Engineering, vol. 1, 1979, pp. 201–207.

Ozone as a Cleaner Touted for Bulk Tanks, Susan Stone, Southern Dairy, Jun. 1993, p. 24.

Cleaning Chemicals—State of the Knowledge in 1985, David R. Kane et al., Diversey Wyandotte Inc., Canada, pp. 312–335 (1985).

Sanitising Treatments for CIP Post–Rinses Brewing and Distilling International, Mar. 1990, pp. 24–25.

Ozone as a Disinfectant in Process Plant, T. R. Bott, Food Control, Jan. 1991, pp. 44–49.

Ozone, The Add–Nothing Sterilant, Robert I. Tenney, Technical Quarterly, Jan.–Mar. 1973, pp. 35–41.

*Primary Examiner*—Allen J. Robinson
*Attorney, Agent, or Firm*—Merchant, Gould, Smith, Edell, Welter & Schmidt, P.A.

[57] ABSTRACT

A cleaning and sanitizing method for soiled solid surfaces, especially clean-in-place process facilities, is described which involves contacting the surfaces first with an aqueous ozone cleaning composition having a pH greater than 7, wherein the ozone is generated by electrical discharge, then quenching the excess ozone and simultaneously sanitizing the surfaces by contact with an aqueous composition containing hydrogen peroxide, a $C_1$–$C_{10}$ peroxyaliphatic carboxylic acid or a mixture thereof.

27 Claims, 4 Drawing Sheets

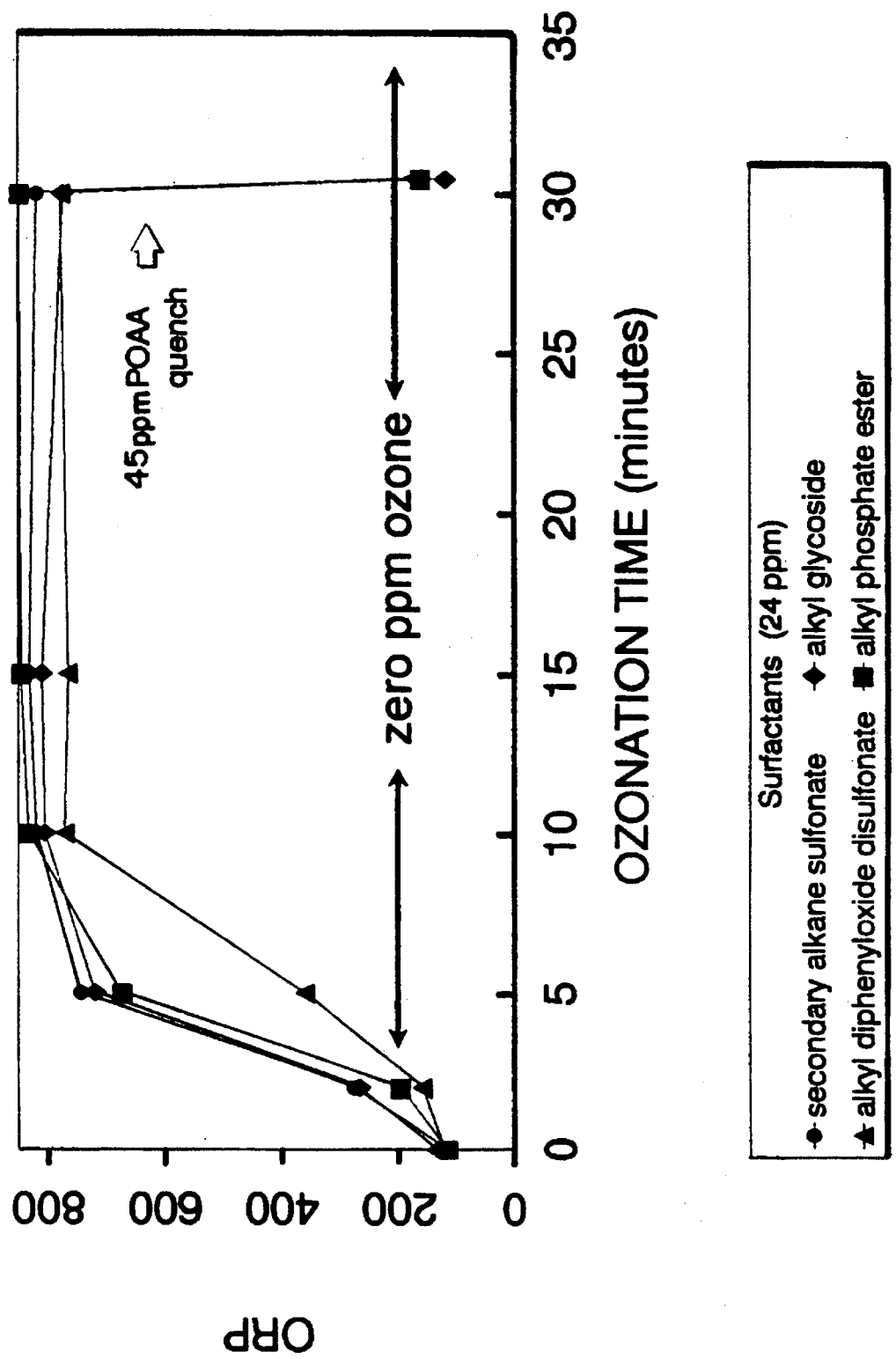

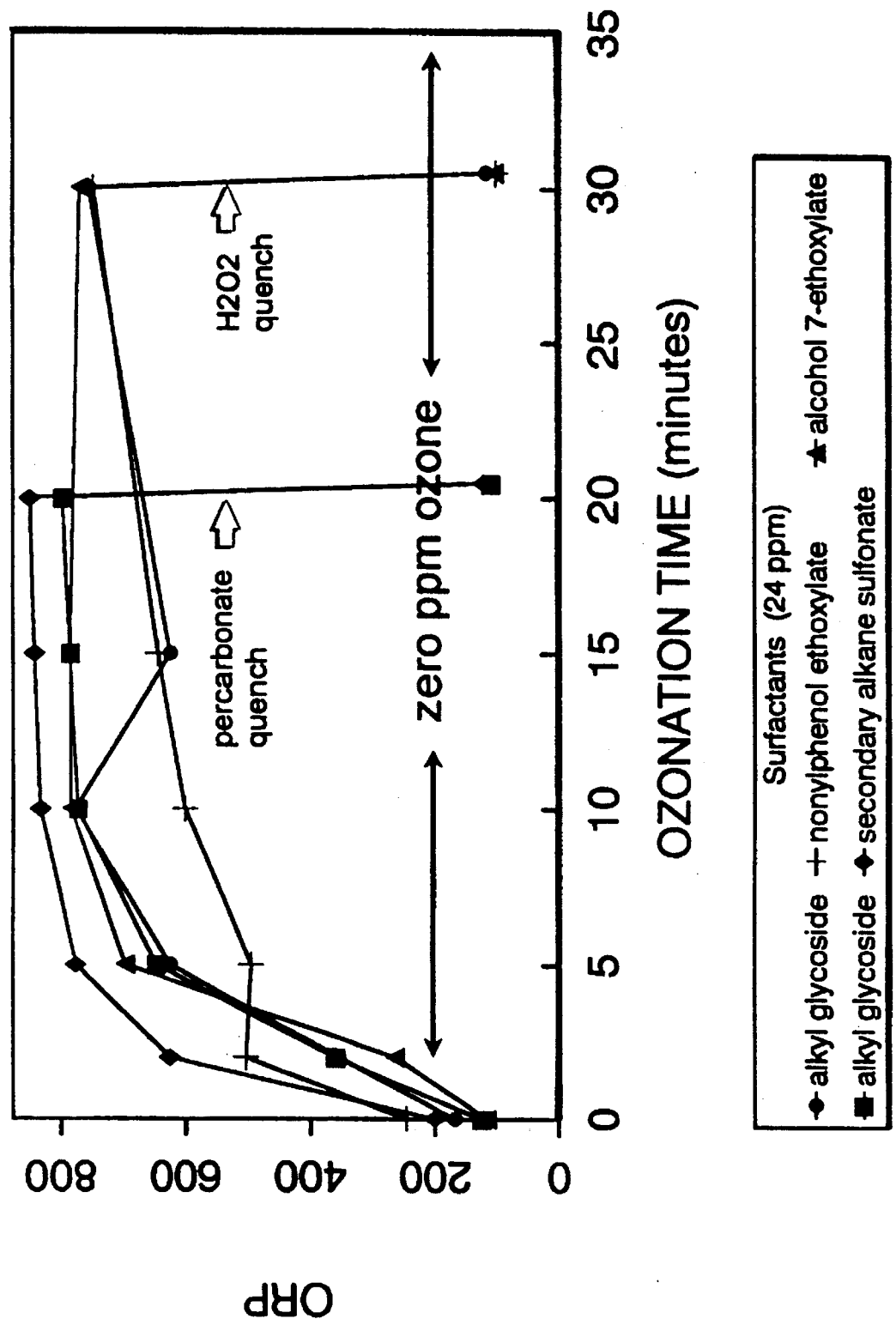

POTENTIATED AQUEOUS OZONE CLEANING AND SANITIZING COMPOSITION FOR REMOVAL OF A CONTAMINATING SOIL FROM A SURFACE

CROSS-REFERENCE TO RELATED APPLICATION

This patent application is a continuation-in-part of U.S. Ser. No. 08/114,193, filed Aug. 20, 1993, now U.S. Pat. No. 5,484,549.

FIELD OF THE INVENTION

The invention relates to an aqueous cleaning and sanitizing composition. The invention also relates to a method for cleaning a soil, from a surface, that can be a tenacious, contaminating residue or film, such as that derived from an organic or food source followed by sanitizing the cleaned surface. More particularly, this invention relates to using either active ozone at a pH greater than 7 or using active ozone potentiated by an additive composition, for the removal of a proteinaceous, fatty or carbohydrate containing soil residue or film from a solid surface followed by quenching the excess ozone and simultaneously sanitizing the solid surface using an aqueous hydrogen peroxide and/or peroxyacid composition.

BACKGROUND OF THE INVENTION

Ozone is an effective biocide and has been widely used for sanitizing, and disinfection in water treatment, beverage and food service markets. In our copending parent application, we have described that ozone dissolved in water containing a Lewis basis can effectively remove protein films on stainless steel and other hard surfaces. A more detailed description is also provided in the present application on this aspect. Nevertheless, a major concern in applying aqueous ozone for cleaning or sanitizing is the excess free ozone in the immediate environment and the related worker exposure hazard.

Thus, although ozone has been demonstrated to be effective in cleaning soil from solid surfaces in plant facilities and in clean-in-place process facilities, there is a need in the industry to reduce the health hazard to workers due to inhalation or contacting with ozone by reducing the level of ozone in the immediate vicinity of application.

SUMMARY OF THE INVENTION

The present invention is based on the discovery that such health hazards and levels of ozone can be minimized and reduced while simultaneously applying further effective sanitizing on the surfaces cleaned by the ozone process. This can be accomplished by application of an aqueous hydrogen peroxide and/or peroxyacid composition which effectively quenches the excess ozone present and simultaneously sanitizes the surfaces treated.

Accordingly, the present invention is directed to a method of cleaning and sanitizing solid surfaces comprising (a) contacting a soil or film residue on a solid surface with an ozonized cleaning aqueous composition having a pH of at least about 7.5 and comprising an effective concentration of an active ozone composition sufficient to produce an oxidation-reduction potential of at least about +550 mV with respect to an Ag/Agcl reference electrode;

(b) treating the contacted solid surfaces with an aqueous sanitizing composition comprising an effective amount of hydrogen peroxide, a $C_1$-$C_{10}$ peroxyaliphatic carboxylic acid or a mixture thereof sufficient to reduce the oxidation-reduction potential below about +400 mV.

In a second aspect of the present invention, there is provided also a method of cleaning and sanitizing substantially fixed in-place process facilities comprising the steps of:

(a) circulating an ozonized cleaning aqueous composition having a pH of at least 7.5 and comprising an effective concentration of an active ozone composition sufficient to produce an oxidation-reduction potential of at least about +550 mV with respect to an Ag/Agcl reference electrode;

(b) circulating an aqueous sanitizing composition comprising an effective amount of hydrogen peroxide, a $C_1$-$C_{10}$ peroxyaliphatic carboxylic acid or a mixture thereof sufficient to reduce the oxidation-reduction potential below about +400 mV.

BRIEF DESCRIPTION OF THE DRAWINGS

FIG. 2 and FIG. 3 illustrate peracid quenching of ozone cleaning systems by plotting oxidation reduction potential (ORP) vs. ozonation time upon the addition of 91 ppm peroxyacetic acid and 45 ppm of peroxyacetic acid respectively.

FIG. 4 is a plot of oxidation reduction potential (ORP) vs. ozone time to illustrate the ozone quenching effect of using common peroxygen bleaches.

DETAILED DESCRIPTION OF THE INVENTION

Figure 1:
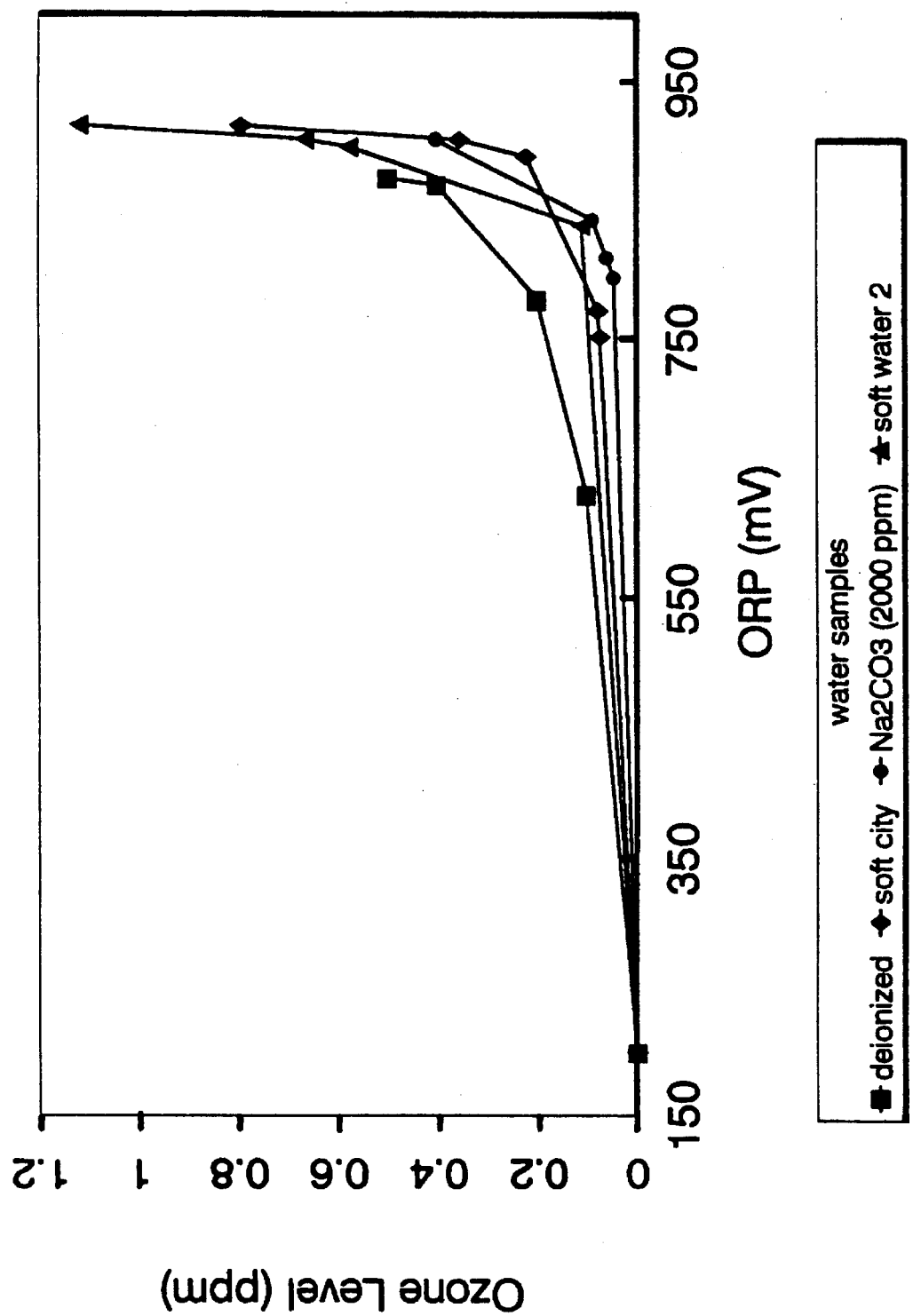
FIG. 1 is a plot of ozone level v. oxidation reduction potential for various aqueous-ozone cleaning systems.

Briefly, the cleaning step method for cleaning hard surfaces uses compositions containing alkaline aqueous ozone. The aqueous ozone compositions can be potentiated by a Lewis base. The cleaning materials of the invention show a surprising level of cleaning properties when used at a basic pH greater than 7.0, when compared to other cleaners and to cleaners using ozone at acidic to neutral pH's. Preferably, the pH of the materials are greater than 7.5 and most preferably greater than 8.0, but less than 13. The Lewis base potentiating compounds useful in the invention comprise a variety of chemical additive materials that can increase the cleaning effect of aqueous ozone solutions.

We have found that the cleaning effect of the ozonized cleaning solution improves as the pH increases. The cleaning action of the cleaning solution is further increased by the addition of a Lewis base into the cleaning solution. A Lewis base is a substance containing an atom capable of donating a pair of electrons to an acid.

Typically ozone can be added to an alkaline solution at a pH above 7.5. The aqueous solution can be made alkaline through the addition of a base. Such bases include alkaline metal hydroxides such as sodium hydroxide, potassium hydroxide, ammonium hydroxide, etc. An alkaline potentiator is a compound that can produce a pH greater than 7 when used in aqueous solution with ozone; or a neutral potentiator can be used at an alkaline pH which can be combined with ozone. These potentiator additives can be used along with, or in place of, the aforementioned hydroxide bases as long as they produce a pH greater than 7. Examples of such materials include alkaline metal carbonates such as sodium carbonate and potassium carbonate or their bicarbonates, and alkaline metal phosphates and alkaline metal silicates such as ortho or polyphosphates and ortho or polysilicates of sodium or potassium. These potentiators can be added as chemical adjuvants to the aqueous medium, or can come from natural sources such as mineral waters. Other examples of potentiators include hydrogen peroxide, and short-chain $C_{3-6}$ branched alcohols. Typically a pH of 7.5 would be effective for the cleaning effect of the ozonized cleaning solution. Preferably, a pH of higher than 8.0 can be used to lead to a better result. A pH greater than 13.5 is likely not to be effective. Most importantly, an oxidation potential of greater than +550 mV (relative to a Ag/AgCl reference electrode) is needed for cleaning at a pH within the effective range.

In aqueous ozone cleaners which comprise sodium or potassium hydroxide as the primary source of alkalinity, it has been found highly preferable to employ about 0.0025–3.0% of the basic materials.

The inorganic alkali content of the alkaline ozone cleaners of this invention is preferably derived from sodium or potassium hydroxide which can be derived from either liquid (about 10 to 60 wt-% aqueous solution) or solid (powdered or pellet) form. The preferred form is commercially-available aqueous sodium hydroxide, which can be obtained in concentrations of about 50 wt-% and in a variety of solid forms of varying particle size.

For many cleaning applications, it is desirable to replace a part or all of the alkali metal hydroxide with: (1) an alkali metal silicate or polysilicate such as anhydrous sodium ortho or metasilicate, (2) an alkali metal carbonate or bicarbonate such as anhydrous sodium bicarbonate, (3) an alkali metal phosphate or polyphosphate such as disodium monohydrogen phosphate or pentasodium tripolyphosphate. This can be done by the direct addition of these chemical adjuvants, or by use of natural waters containing these materials as natural minerals. When incorporated into the chemical composition within the preferred temperature ranges these adjuvants can act as an adjunct caustic agent, protect metal surfaces against corrosion, and sequester hardness metal ions in solution.

Sequestering agents can be used to treat hardness ions in service water, such ions include calcium, manganese, iron and magnesium ions in solution, thereby preventing them from interfering with the cleaning materials and from binding proteins more tightly to solid surfaces. Generally, a sequestrant is a substance that forms a coordination complex with a di or tri-valent metallic ion, thereby preventing the metallic ion from exhibiting its usual undesirable reactions. Chelants hold a metallic ion in solution by forming a ring structure with the metallic ion. Some chelating agents may contain three or four or more donor atoms that can coordinate simultaneously to hold a metallic ion. These are referred to as tridentate, tetradentate, or polydentate coordinators. The increased number of coordinators binding to a metallic ion increases the stability of the complex. These sequestrants include organic and inorganic and polymeric species.

In the present compositions, the sodium condensed phosphate hardness sequestering agent component functions as a water softener, a cleaner, and a detergent builder. Alkali metal (M) linear and cyclic condensed phosphates commonly have a $M_2O:P_2O_5$ mole ratio of about 1:1 TO 2:1 and greater. Typical polyphosphates of this kind are the preferred sodium tripolyphosphate, sodium hexametaphosphate, sodium metaphosphate as well as corresponding potassium salts of these phosphates and mixtures thereof. The particle size of the phosphate is not critical, and any finely divided or granular commercially available product can be employed.

Sodium tripolyphosphate is the most preferred hardness sequestering agent for reasons of its ease of availability, low cost, and high cleaning power. Sodium tripolyphosphate (STPP) acts to sequester calcium and/or magnesium cations, providing water softening properties. STPP contributes to the removal of soil from hard surfaces and keeps soil in suspension. STPP has little corrosive action on common surface materials and is low in cost compared to other water conditioners. If an aqueous concentration of tripolyphosphate is desired, the potassium salt or a mixed sodium potassium system should be used since the solubility of sodium tripolyphosphate is 14 wt% in water and the concentration of the tripolyphosphate concentration must be increased using means other than solubility.

The ozone detergents can be formulated to contain effective amounts of synthetic organic surfactants and/or wetting agents. The surfactants and softeners must be selected so as to be stable and chemically-compatible in the presence of ozone and alkaline builder salts. One class of preferred surfactants is the anionic synthetic detergents. This class of synthetic detergents can be broadly described as the water-soluble salts, particularly the alkali metal (sodium, potassium, etc.) salts, or organic sulfuric reaction products having in the molecular structure an alkyl radical containing from about eight to about 22 carbon atoms and a radical selected from the group consisting of sulfonic acid and sulfuric acid ester radicals.

Preferred anionic organic surfactants contain carboxylates, sulfates, phosphates (and phosphonates) or sulfonate groups. Preferred sulfates and sulfonates include alkali metal (sodium, potassium, lithium) primary or secondary alkane sulfonates, alkali metal alkyl sulfates, and mixtures thereof, wherein the alkyl group is of straight or branched chain configuration and contains about nine to about 18 carbon atoms. Specific compounds preferred from the standpoints of superior performance characteristics and ready availability include the following: sodium decyl sulfonate, sodium dodecyl sulfonate, sodium tridecyl sulfonate, sodium tetradecyl sulfonate, sodium hexadecyl sulfonate, sodium octadecyl sulfate, sodium hexadecyl sulfate and sodium tetradecyl sulfate. Carboxylate surfactants can also be used in the materials of the invention. Soaps represent the most common of commercial carboxylates. Additional carboxylate materials include alphasulfocarboxylic acid esters, polyalkoxycarboxylates and acyl sarcocinates. The mono and diesters and orthophosphoric acid and their salts can be useful surfactants. Quaternary ammonium salt surfactants are also useful in the compositions of the invention. The quaternary ammonium ion is a stronger hydrophile than primary, secondary or tertiary amino groups, and is more stable to ozonolysis. Preferred quaternary surfactants include substantially those stable in contact with ozone including $C_{6-24}$ alkyl trimethyl ammonium chloride, $C_{8-10}$ dialkyl dimethyl ammonium chloride, $C_{6-24}$ alkyl-dimethylbenzyl ammonium chloride, $C_{6-24}$ alkyl-dimethyl amine oxides, $C_{6-24}$ dialkyl-methyl amine oxides, $C_{6-24}$ trialkyl amine oxides, etc.

Nonionic synthetic surfactants may also be employed, either alone or in combination with anionic and cationic types. This class of synthetic detergents may be broadly defined as compounds produced by the condensation of alkylene oxide or polyglycoside groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water soluble or dispersible compound having the desired degree of balance between hydrophilic and hydrophobic elements.

For example, a well-known class of nonionic synthetic detergents is made available on the market under the trade name of "Pluronic". These compounds are formed by condensing ethylene oxide with a hydrophobic base formed by the condensation of propylene oxide with propylene glycol. The hydrophobic portion of the molecule has a molecular weight of from about 1,000 to 1,800. The addition of polyoxyethylene radicals to this hydrophobic portion tends to increase the water solubility of the molecule as a whole and the liquid character of the products is retained up to the point where the polyoxyethylene content is about 50 percent of the total weight of the condensation product. Another example of nonionic detergents with noted stability during the cleaning procedure are the class of materials on the market under the tradename of APG-polyglycosides. These nonionic surfactants are based on glucose and fatty alcohols.

Other suitable nonionic synthetic detergents include the polyalkylene oxide condensates of alkyl phenols, the products derived from the condensation of ethylene oxide or propylene oxide with the reaction product of propylene oxide and ethylene diamine, the condensation product of aliphatic fatty alcohols with ethylene oxide as well as amine oxides and phosphine oxides.

Ozone cannot be easily stored or shipped. Ozone is typically generated on site and dissolved into aqueous medium at the use locus just prior to use. Within practical limits, shortening the distance between points of generation and use reduce the decomposition loss of the concentration of ozone in the material. The half life of ozone in neutral solutions is on the order to 3–10 minutes and less as pH increases. Weak concentrations of ozone may be generated using ultraviolet radiation. Typical production of ozone is made using electrical corona discharge. The process involves the case of a source of oxygen in a pure $O_2$ form, generally atmospheric oxygen (air), or enriched air. The source of $O_2$ is passed between electrodes across which a high voltage alternating potential is maintained. The electrodes are powered from a step transformer using service current. The potential is established across the electrodes which are configured to prevent arcing. As oxygen molecules enter the area of the potential, a corona is created having a proportion of free atomic oxygen ions from dissociated $O_2$. The high energy atomic ions (O) when combined with oxygen ($O_2$) form a mixture of oxygen and ozone. These generators are available commercially. The ozone containing gaseous mixture is generally directly contacted with an aqueous solution through bubbling or other gas dispersion techniques to introduce a concentration of ozone into the aqueous medium. The contact between water and the aqueous medium is engineered to maximize the absorption of ozone when compared to the rate of decomposition of ozone in the alkaline aqueous medium and the required ozone concentration of the water.

The activity of ozone in the materials of the invention can be improved by introducing ozone into the smallest possible diameter bubble formation. Small bubbles promote the mass transfer of ozone into aqueous solution. Additionally, surface active agents which lower the gas-liquid interfacial tension can be used to enhance ozone gas transport to the aqueous medium. Rapid dissolution of ozone can reduce the tendency to off gas, and cause reactions with solution components to produce oxidized species and promote the effective use of ozone. Alternately, the $O_3$ can be produced using ultraviolet light or combinations of these methods. Neutral aqueous solutions have a small but measurable solubility of ozone at various temperatures; these are:

| Temperature | Ozone Concentration |
|---|---|
| 0° C. | 35 (ppm) |
| 20° C. | 21 |
| 40° C. | 4 |
| 60° C. | 0 |

The stability of ozone in aqueous solution decreases as alkalinity rises. The half life of ozone in 1 N sodium hydroxide is <10 seconds. For the purpose of the invention involving concentrations of ozone in aqueous solution, the term "total ozone" relates to the amount of ozone added to the aqueous phase from the gas phase. Typically, these "total ozone" levels in the gas phase are 0.1–3.0 wt %. "Measured ozone" is the apparent concentration of ozone (as $O_3$) in aqueous solution. These aqueous levels are about 0.1–22.2 mg/L (ppm). The difference between total ozone and measured ozone relates to an amount of ozone that apparently becomes stored in aqueous solution by reaction with inorganic species to form ozonized or oxidized inorganic materials, e.g., hydroxyl radicals, ozonide radical ion, superoxide radical ion, etc. Such oxidized materials tend to be a source of oxidizing potential. We have found that the cleaning power of the materials of the invention relate to the presence of free solubilized "measured" ozone species and the presence of species that can act as oxidizing agents created in-situ by the reaction of ozone with materials in solution. The term "active" ozone composition refers to the total concentration of oxidizing species (organic and inorganic) produced by introducing ozone into the formulated cleaners of the invention. The term "initial ozone" means the measured concentration of ozone immediately after introduction of ozone into the aqueous solution. The difference between initial ozone and measured ozone relates to timing of the measurement. Measured ozone is the concentration of ozone in solution measured at any time after an initial value is found.

In aqueous cleaning compositions using ozone, the concentration of the ozone, and oxidizing ozone byproducts, should be maintained as high as possible to obtain the most active cleaning and antimicrobial properties. Accordingly, a concentration as high as 23 parts by weight of ozone per million parts of total cleaning solution is a desirable goal. Due to the decomposition of ozone and the limited solubility of ozone in water, the concentration of the materials commonly fall between about 0.1 and 10 parts of ozone per million parts of aqueous cleaning solution, and preferably from about 1.0 to about 5 parts per million of ozone in the aqueous material. The oxidizing potential of this solution, as measured by a standard, commercially available, ORP (oxidation-reduction potential) probe, is between +350 and 1500 mV (as referenced to a standard Ag/AgCl electrode), and is dependent on the pH of the solution. Most importantly, an ORP greater than +550 mV is necessary for proper cleaning.

The Lewis base additive materials used in the invention to potentiate the action of ozone can be placed into the water stream into which ozone is directed for preparing the ozone materials or can be post added to the aqueous stream.

The total concentration of ozone potentiators used in the use solution containing ozone can range from about 10 parts per million to about 3000 parts per million (0.3 wt %). The material in use concentrations typically fall between 50 and 3000 parts per million, and preferably 300–1000 ppm of the active ozone potentiators in the aqueous cleaning solutions. In the preferred ozone containing aqueous systems of the invention, inorganic potentiators are preferred due to the tendency of organic materials to be oxidized by the active ozone containing materials.

In use the aqueous materials are typically contacted with soiled target surfaces. Such surfaces can be found on exposed environmental surfaces such as tables, floors, walls, can be found on ware including pots, pans, knives, forks, spoons, plates, dishes, food preparation equipment; tanks, vats, lines, pumps, hoses, and other process equipment. One preferred application of the materials of the invention relates to dairy processing equipment. Such equipment are commonly made from glass or stainless steel. Such equipment can be found both in dairy farm installations and in dairy plant installations for the processing of milk, cheese, ice cream or other dairy products.

The ozone containing aqueous cleaning material can be contacted with soiled surfaces using virtually any known processing technique. The material can be sprayed onto the surface, surfaces can be dipped into the aqueous material, the aqueous cleaning material can be used in automatic warewashing machines or other batch-type processing. A preferred mode of utilizing the aqueous ozone containing materials is in continuous processing, wherein the ozone containing material is pumped through processing equipment and CIP (clean in place) processing. In such processing, an initial aqueous rinse is passed through the processing equipment followed by a sanitizing cleaning using the potentiated ozone containing aqueous materials. The flow rate of the material through the equipment is dependent on the equipment configuration and pump size. Flow rates on the order of 10 to 150 gallons per minute are common. The material is commonly contacted with the hard surfaces at temperatures of about ambient to 70° C. We have found that to achieve complete sanitizing and cleaning that the material should be contacted with the soiled surfaces for at least 3 minutes, preferably 10 to 45 minutes at common processing pressures.

We have found that combining ozone with a Lewis base in an aqueous solution at a pH greater than 7, preferably greater than 8, results in surprisingly improved cleaning properties. A variety of available detergent components have been found that potentiate the effectiveness of ozone in cleaning surfaces and in particular removing proteinaceous soils from hard surfaces. The results are surprising in view of the fact that substantially complete cleaning has resulted at conditions including room temperature (74° F.), 10 minute contact time and moderate pH's ranging between 8 and 13 (U.S. typical CIP programs of 160° F., 30–40 minutes, a pH greater than 12, and hypochlorite greater than 100 ppm). In all the systems studied, raising the pH from 8 to 13 can greatly enhance the cleaning effect. This effect is clearly shown in Examples 1–8.

The data in the Examples were obtained in experiments we performed that demonstrate the effectiveness of ozonized solutions as cleaning agents. Polished 304 stainless steel coupons of sizes 3"X5" and 1"X3" were cleaned according to a standard CIP protocol for the data generated. The following cleaning protocol was used. New stainless steel surfaces were treated by first rinsing the steel in 100°–115° F. water for 10 minutes. The rinsed surfaces were washed in an aqueous composition containing vol % of a product containing 0.28% cellosize, 6% linear alkyl benzene sulfonate (60 wt % aqueous active), sodium xylene sulfonate (40 wt % aqueous active), ethylene diamine tetraacetic acid (40 wt % aqueous active), 6% sodium hydroxide, 10 wt % propylene glycol methyl ether (the balance of water). Along with 1.5 vol % of an antifoam solution comprising 75 wt % of a benzylated polyethoxy polypropoxy block copolymer and 25 wt % of a nonyl phenol alkoxylate wherein the alkoxylate moiety contains 12.5 mole % ethylene oxide and 15 mole % propylene oxide. After washing the surfaces at 110°–115° F. for 45 minutes, the surfaces are rinsed in cold water and passivated by an acid wash in a 54% by volume solution of a product containing 30 wt % of phosphoric acid (75 wt % active aqueous) and 34% nitric acid (42° baume). After contact with the acid solution, the coupons are rinsed in cold water.

The cleaned coupons were then immersed in cold (40° F.) milk while the milk level was lowered at a rate of 4 feet per hour by draining the milk from the bottom. The coupons were then washed in a consumer dishwasher under the following conditions:

Cleaning cycle: 100° F., 3 minutes, using 10 gallons of city water containing by weight 60 ppm Calcium and 20 ppm Magnesium (both as chloride salt) and 0.26% of the detergent Principal with a reduced level (30 ppm) of sodium hypochlorite.

Rinsing cycle: 100° F., 3 minutes, using 10 gallons of city water.

The procedure of soiling and washing was repeated for 20 cycles. The films produced after the 20 cycles were characterized to verify the presence of protein on the coupons. Reflectance infrared spectra showed amide I and amide II bands, which are characteristic of proteinaceous materials. Scanning electron microscope photomicrographs showed greater intensity of soiling along the grains resulted from polishing. Energy Dispersive X-ray Fluoresenic Spectroscopy, EDS, showed the presence of carbon and oxygen, indicative of organic materials. Staining with Coomassie Blue gave a blue color, typical of a proteinaceous material.

These soils were demonstrated to be tenacious soils. A typical cleaning regimen could not remove the soil. A severe cleaning protocol could remove the soil. As a control, spot testing and washing the coupons showed that washing for 3 minutes in a dishwasher at 100° F. with 0.4% Principal (2000 ppm of sodium hydroxide, 2000 ppm of sodium tripolyphosphate, and 200 ppm of sodium hypochlorite) did not produce any substantial cleaning effect. As a further control, in more severe cleaning conditions such as 1% Principal for 90 minutes appeared to be effective in cleaning the soil film.

In addition, protein soiled coffee cups were obtained from a restaurant. Infrared spectra, scanning electron microscopy (SEM) and Coomassie Blue staining were used to characterize the soils. A similar cleaning protocol as above demonstrated the tenacity of the film and little soil removal was found in 10 minutes of cleaning. The SEM pictures after cleaning with hypochlorite solutions showed the soil was not removed, but merely bleached to lose visible coloration.

Protein Cleaning Procedure

The cleaning procedure utilizing ozone is described in the following:

Ozone is generated through electrical discharges in air or oxygen. An alternate method would be to generate the ozone with ultraviolet light, or by a combination of these methods. The generated ozone, together with air, is injected through a hose into a carrier solution, which might be either a buffered, or unbuffered, alkaline aqueous medium or a buffered, or unbuffered, aqueous medium containing the ozone potentiator. The injection is done using either an in-line mixing educator, or by a contact tower using a bubble diffusion grid; however, any type of gas-liquid mixer would work as well. A continuous monitor of the level of oxidation power of the solution is performed using a conventional ORP (oxidation-reduction potential) probe; the solution was typically mixed with ozone until the ORP reading reached +550 mV relative to a standard Ag/AgCl reference electrode. Additionally, samples can be drawn and measured by traditional analytical techniques for determining aqueous ozone concentrations. The solution can be pumped directly to the spray site with the gas, or to a holding tank where the activated liquid is bled off and sprayed, or poured, onto the surfaces of coupons to be cleaned. Both processes were used successfully, and a pump can be used to drive the cleaning solution through a nozzle to form a spray. The operational parameters are variable, but the ones most typically used are: gas flow rate of 20–225 SCFH, a liquid pumping rate of 0.075–3 gal/min, temperatures of 50°–100° F., pH's of 7.5 to 13.5, spraying times of 0–30 minutes and an ORP of +550 to 1500 mV. These parameters are scaleable to greater or lesser rates depending on the scale of the system to be cleaned. For example, longer cleaning times (35–60 minutes) can be used when lower levels of aqueous ozone are employed. As a control, air—without ozone—was injected into the solutions listed as non-ozone (air) studies.

After cleaning, the cleanliness of the coupons were evaluated by a visual inspection, reflectance measurements, infrared spectrometry, and dyeing with Coomassie Blue (a protein binding dye).

By visual inspection the soiled stainless steel coupons are seen to have a yellow-bluish to brownish decolorization, with considerable loss in reflection. When cleaned the coupons become very reflective and the off colorization is removed.

Reflectance is a numerical representation of the fraction of the incident light that is reflected by the surface. These measurements were done on a Hunter Ultrascan Sphere Spectrocolorimeter (Hunter Lab). Cleanliness of the surface is related to an increase in the L-value (a measurement of the lightness that varies from 100 for perfect white to 0 for black, approximately as the eye would evaluate it, and the whiteness index (WI) (a measure of the degree of departure of an object from a 'perfect' white). Both values have been found as very reproducible, and numerically representative of the results from visual inspection. Consistently it is found that a new, passivated, stainless steel coupon has an L value in the range of 75–77 (usually 76±1), and a WI value of 38–42 (usually 40±1). After soiling with the aforementioned protein soiling process, the L value is about 61 and the WI around 10). It is shown that effective and complete cleaning will return the L and WI values to those at, or above, the new coupon values. Lack of cleaning, or removal to intermediate levels, gave no, to intermediate, increases in the reflectance values, respectfully.

Infrared chemical analysis using grazing angles of reflection were used to verify the presence (during the soiling process), and removal (during the cleaning process), of proteins from the surfaces. The IR data for a typical soiled coupon was found to have an amide-I carbonyl band of greater than 30 milli-Absorbance (mA) units, while an 80% cleaned sample (determined via reflectometry) would be much less than 5 units. Further removal to 95% dropped the IR absorption to less than 1 mA unit. Accordingly, the data verifies the removal of the protein, rather than mere bleaching and decolorization of the soil.

The Coomassie Blue dyeing is a recognized qualitative spot test for the presence of proteinaceous material. Proteinaceous residue on a surface of an item shows up as a blue color after being exposed to the dye, while clean surfaces show no retention of the blue coloration.

The Quenching and Sanitizing Step

Following the ozone cleaning step, the excess ozone can be quenched rapidly by injection of quenchers into the liquid stream prior to the spray into the liquid stream. The present invention applies onto the ozone cleaned surfaces a composition which not only quenches the ozone but simultaneously acts as a sanitizer. Thus, the second step is the contact of the cleaned surfaces or clean in-place process facilities with an aqueous sanitizing composition comprising an effective amount of hydrogen peroxide, peroxyacid, namely a $C_1$–$C_{10}$ peroxyaliphatic carboxylic acid or a mixture thereof. This application allows the ozonated aqueous solutions to clean proteinaceous soils in clean-in-place systems, followed by a deactivation step where ozone is rapidly removed and simultaneous sanitizing occurs.

Thus, the application of hydrogen peroxide, a $C_1$–$C_{10}$ peroxyaliphatic carboxylic acid or a mixture thereof affords not only surprising effective quenching of ozone but simultaneous sanitizing of the solid surfaces.

The peroxyaliphatic carboxylic acid can be any one from $C_1$–$C_{10}$ of the aliphatic peroxymonocarboxylic, peroxydicarboxylic or peroxytricarboxylic acids such as, for example, peroxyacetic, peroxypropionic, peroxyglycolic, peroxysuccinic, peroxyglutaric, peroxycitric, peroxyoctanoic and the like and mixtures thereof. Preferred are peroxyacetic, peroxyglutaric and peroxyoctanoic or mixtures thereof. The most preferred is peroxyacetic acid.

The sanitizing composition containing such peroxyacid in the treatment of the surfaces must be present in at least about ten parts per million (ppm).

The peroxycarboxylic acid composition may also contain corresponding carboxylic acids of $C_1$–$C_{10}$ carbon atoms. These are aliphatic mono-, di- or tri-carboxylic acids such as, for example, acetic acid, propionic acid, glycolic acid, succinic acid, glutaric acid, citric acid, octanoic acid and the like and mixtures thereof. A preferred carboxylic acid is acetic acid, glutaric acid or octanoic acid or mixtures thereof. Most preferred in the composition is octanoic acid.

Thus, a preferred composition may contain a combination of approximately about 10–150 ppm of a $C_1$–$C_{10}$ peroxyaliphatic carboxylic acid, about 0–25 ppm of octanoic acid, and about 2–200 ppm of hydrogen peroxide.

The above peroxyacids provide antibacterial activity against a wide variety of microorganisms, such as gram positive (e.g., *Staphylococcus aureus*) and gram negative (e.g., *Escherichia coli*) microorganisms, yeast, molds, bacterial spores, etc.

The antimicrobial concentrate of the present invention can comprise about 0.1 to 25 wt-%, preferably about 1 to 15 wt-%, and most preferably about 5 to 15 wt-% of $C_1$–$C_{10}$ peroxyacids. The concentrate contains sufficient acid so that the end use solution has a pH of about 1 to 8, preferably about 3 to 7. Some acidity may come from an inert acidulant which may be optionally added (e.g., phosphoric acid).

The peracid components used in the composition of the invention can be produced in a simple manner by mixing a hydrogen peroxide ($H_2O_2$) solution with the desired amount of acid. With the higher molecular weight fatty acids, a hydrotrope coupler may be required to help solubilize the fatty acid. The $H_2O_2$ solution also can be added to previously made peracids such as peracetic acid or various perfatty acids to produce the peracid composition. The concentrate can contain about 1 to 70 wt-%, preferably about 5 to 30 wt-% of hydrogen peroxide.

The concentrate composition can further comprise a free $C_1$–$C_{10}$ carboxylic acid, or mixtures thereof as mentioned above. The free $C_1$–$C_{10}$ carboxylic acid can be present as a result of an equilibrium reaction with the hydrogen peroxide to form the peroxyacids.

Optional components various optional materials may be added to the composition of the invention to help solubilize the fatty acids, restrict or enhance the formation of foam, to control hard water, to stabilize the composition, or to further enhance the antimicrobial activity of the composition.

The composition of the invention can contain a surfactant hydrotrope coupling agent or solubilizer that permits blending short chain perfatty acids in aqueous liquids. Functionally speaking, the suitable couplers which can be employed are non-toxic and retain the fatty acid and the perfatty acid in aqueous solution throughout the temperature range and concentration to which a concentrate or any use solution is exposed.

Any hydrotrope coupler may be used provided it does not react with the other components of the composition or negatively affect the antimicrobial properties of the composition. Representative classes of hydrotropic coupling agents or solubilizers which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters) and $C_8$–$C_{10}$ alkyl glucosides. Preferred coupling agents for use in the present invention include noctanesulfonate, available as NAS 8D from Ecolab, and the commonly available aromatic sulfonates such as the alkyl benzene sulfonates (e.g. xylene sulfonates) or naphthalene sulfonates.

Some of the above hydrotropic coupling agents independently exhibit antimicrobial activity at low pH. This adds to the efficacy of the present invention, but is not the primary criterion used in selecting an appropriate coupling agent. Since it is the presence of perfatty acid in the protonated neutral state which provides biocidal activity, the coupling agent should be selected not for its independent antimicrobial activity but for its ability to provide effective interaction between the substantially insoluble perfatty acids described herein and the microorganisms which the present composition control.

The hydrotrope coupling agent can comprise about 1 to 30 wt-%, preferably about 1 to 20 wt-%, and most preferably about 2 to 15 wt-% of the concentrate composition.

Compounds such as mono, di and trialkyl phosphate esters may be added to the composition to suppress foam. Such phosphate esters would generally be produced from aliphatic linear alcohols, there being from 8 to 12 carbon atoms in the aliphatic portions of the alkyl phosphate esters. Alkyl phosphate esters possess some antimicrobial activity in their own right under the conditions of the present invention. This antimicrobial activity also tends to add to the overall antimicrobial activity of the present compositions even though the phosphate esters may be added for other reasons. Furthermore, the addition of nonionic surfactants would tend to reduce foam formation herein. Such materials tend to enhance performance of the other components of the composition, particularly in cold or soft water. A particularly useful nonionic surfactant for use as a defoamer is nonylphenol having an average of 12 moles of ethylene oxide condenses thereon, it being encapped with a hydrophobic portion comprising an average of 30 moles of propylene oxide.

Chelating agents can be added to the composition of the invention to enhance biological activity, cleaning performance and stability of the peroxyacids. For example, 1-hydroxyethylidene-1,1-diphosphonic acid commercially available from the Monsanto Company under the designation "DEQUEST" has been found to be effective. Chelating agents can be added to the present composition to control or sequester hardness ions such as calcium and magnesium. In this manner both detergency and sanitization capability can be enhanced.

Other materials which are sufficiently stable at the low pH contemplated by the present composition may be added to the composition to impart desirable qualities depending upon the intended ultimate use. For example, phosphoric acid ($H_3PO_4$) can be added to the composition of the invention. Additional compounds can be added to the concentrate (and thus ultimately to the use solution) to change its color or odor, to adjust its viscosity, to enhance its thermal (i.e., freeze-thaw) stability or to provide other qualities which tend to make it more marketable.

The composition of the invention can be made by combining by simple mixing of hydrogen peroxide and an effective amount of a $C_1$–$C_{10}$ peroxyacid. A preferred composition of the invention can be made by mixing a $C_1$–$C_{10}$ carboxylic acid, a coupler and a stabilizer and reacting this mixture with hydrogen peroxide. A stable equilibrium mixture is produced containing a $C_1$–$C_{10}$ peroxycarboxylic acid allowing the mixture to stand for from one to seven days at 15° C. to 25° C. As with any aqueous reaction of hydrogen peroxide with a free carboxylic acid, this gives a true equilibrium mixture. In this case, the equilibrium mixture will contain hydrogen peroxide, a $C_1$–$C_{10}$ carboxylic acid, a $C_1$–$C_{10}$ peroxycarboxylic acid, water, and various couplers and stabilizers.

By using the above approach, the composition of the invention can be formulated by merely mixing readily available raw materials, e.g., acetic acid, hydrogen peroxide and fatty acid. By allowing solution time for equilibrium to be obtained, the product containing both of the active biocides is obtained.

Concentrate and Use Compositions

The present invention contemplates a concentrate composition which is diluted to a use solution prior to its utilization as a sanitizer and dependent upon the intended dilution factor and desired acidity in the use solution. The $C_1$–$C_{10}$ peroxyacid component is generally obtained by reacting a $C_1$–$C_{10}$ carboxylic acid with hydrogen peroxide. The resulting concentrate is diluted with water to provide the use solution. Generally, a dilution of 1 fluid oz. to 4 gallons (i.e. dilution of 1 to 500 by volume) or to 8 gallons (i.e. dilution of 1 to 1,000 by volume) of water can be obtained with 2% to 20% total peracids in the concentrate. Higher use dilution can be employed if elevated use temperature (greater than 20° C.) or extended exposure time (greater than 30 seconds) are also employed.

In its intended end use, the concentrate is diluted with a major proportion of water and used for purposes of sanitization. The typical concentrate composition described above is diluted with available tap or service water to a formulation of approximately 1 oz. concentrate to 8 gallons of water. An aqueous antimicrobial sanitizing use solution comprises at least about $C_1$–$C_{10}$ ppm, preferably about 20 to 50 ppm of a $C_1$–$C_8$ peroxycarboxylic acid, and at least about 1 ppm, preferably about 2 to 200 ppm of hydrogen peroxide. Preferably the total peracid concentration in the use solution is less than about 75 ppm, and most preferably between about 5 to 50 ppm. Higher levels of peracids can be employed in the use solution to obtain disinfecting or sterilizing results.

The aqueous use solution can further comprise at least about 1 ppm, preferably about 2 to 20 ppm, of hydrotrope coupling agent, and at least about 1 ppm, preferably about 2 to 200 ppm of a free $C_1$–$C_{10}$ carboxylic or mixtures thereof. The aqueous use solution has a pH in the range of about 2 to 8, preferably about 3 to 7.

Methods of Use

As noted above, the present composition is useful in the cleaning or sanitizing of the above described processing facilities or equipment in the food service, food processing or health care industries.

Generally, the actual cleaning of the in-place system or other surface is accomplished as described above with the ozone cleaning step. After this cleaning step, the instant sanitizing composition is applied or introduced into the system at a use solution concentration in unheated, ambient temperature water. The present sanitizing composition is found to remain in solution in cold (e.g., 40° F./4° C.) water and heated (e.g., 140° F./60° C.) water. Although it is not normally necessary to heat the aqueous use solution of the present composition, under some circumstances heating may be a desirable to further enhance its antimicrobial activity.

A method of sanitizing substantially fixed in-place process facilities comprises the following steps. The use composition of the invention is introduced into the process facilities at a temperature in the range of about 4 to 60° C. After introduction of the use solution, the solution is circulated through out the system for a time sufficient to sanitize the process facilities (i.e., to kill undesirable microorganisms). After the system has been sanitized by means of the present composition, the use solution is, if desired, drained from the system. Upon completion of the sanitizing step, the system optionally may be rinsed with other materials such as potable water. The composition is preferably circulated through the process facilities for 10 minutes or less.

As the term "sanitizing" is used in the method of the instant invention, it means a reduction in the population numbers of undesirable microorganism by about 2 powers of 10 or greater (i.e., at least 2 orders of magnitude) after a 30 second exposure time. A 5-log reduction is most preferred. It is to be emphasized that the instant use solution provides cleaning as well as sanitizing performance although its primary utility is sanitizing. The composition may also be used to achieve disinfection or sterilization (i.e., elimination of all microorganisms) by employing higher levels of peracids in the use solution.

The following examples are illustrations of the patent, and are not to be taken as limiting the scope of the application of the patent.

Examples of Ozone Cleaning

The experimental data of Tables 1–8 demonstrates the cleaning effect of ozone. Generally the effectiveness of a cleaning process depends on the pH and ORP values of the cleaning solution. Generally conditions leading to higher amounts of ozone, or any ozone-activated species, as measured by an ORP probe reading, exposure at the cleaning site gave better results; i.e., high fluid flow rates, increased reaction times, high potentiator levels, etc.

EXAMPLE 1

EFFECTS OF pH ON CLEANING

The effect of pH on air and ozone cleaning, of proteinaceous soils, are shown in Table 1. The results demonstrate that the protein soil is not easily removed by the mere addition of air, as the control gas-additive, and typically less than 15% of the soil is removed under any of the experimental conditions (see Table 1, rows 1–13). In contrast to air cleaning, ozone injected under low-to-high (25–10,000 ppm metal hydroxide) alkaline conditions is very effective at protein soil removal under a variety of experimental conditions, yielding relatively high levels of cleaning (see Table 1, rows 19–31); i.e., greater than 95% protein soil removal can be obtained with ozone present when using an assortment of variable experimental conditions including spray time, liquid flow rate, pH, and liquid phase ozone concentration. Generally when ozone is present, many combinations of these conditions will lead to effective soil removal, and increasing any of these aforementioned variables tends to enhance the cleaning. For example, the effect of increasing the liquid spray flow rate and time, on soil removal, is demonstrated by comparing rows 19 and 20, or rows 25–27. By contrast, these variables have little effect when ozone is absent and only air is injected.

The data also demonstrates the lack of effectiveness of ozone for protein soil removal when the pH is at, or below, a pH of 7 (see Table 1, rows 14–18). This is remarkable since acidic conditions are known to favor the stability of ozone in solution, and give a larger oxidation/reduction potential than ozone under alkaline conditions; however, acidic conditions do not appear to favor the protein cleaning power of the mixture. Conversely, the cleaning capacity is enhanced under conditions where ozone is known to be less stable (i.e., alkaline conditions, with the presence of hydroxide ions) and possesses a lower oxidation potential, thus, demonstrating the non-obviousness of the invention.

EXAMPLE 2

EFFECTS OF LEWIS BASE EXAMPLES ON CLEANING

Table 2 illustrates the effect of various Lewis base, pH-increasing, additives on air and ozone cleaning of the proteinaceous soil. This group is selected from the alkali metal hydroxides, alkali metal silicates (or polysilicates), alkali metal phosphates (or polyphosphates), alkali metal borates, and alkali metal carbonates (or bicarbonates), or combinations thereof. The results demonstrate that the protein soil is not easily removed (usually less than 10%) by these additives when air is added to the system (rows 6, 11, 16, 19, 25); however, when ozone is injected (rows 1–5, 7–10, 12–15, 17–18, 20–24, 26–31) these adjuvants are quite effective in assisting protein soil removal, even under alkaline conditions (pH's 8–13) which a skilled artisan would be directed away from in prior art disclosures. Of special novel significance are the studies which allow for very effective soil removal under relatively mild alkalinity (a pH between 8–10) CIP cleaning conditions (e.g. the tripoly system at about pH=9 in lines 7–11, the bicarbonate system at about pH =7.0 in lines 20–27, and the borate system at pH's 7–9 in lines 28–31).

EXAMPLE 3

EFFECTS OF SODIUM BICARBONATE

Table 3 exemplifies the cleaning effect of the Lewis base, sodium bicarbonate, which is naturally present from mineral water (present at 244 ppm in the experiments of Table 3). This data for comparison to making adjuvant additions from commercial chemical sources, and demonstrates the ability to remove proteinaceous soils using ozone and water containing inherent levels of ozonepotentiating Lewis bases. These natural levels of minerals can be used in place of, or as an additive to, the protein cleaning processes using adjuvant levels of chemical mixtures. The data also indicates that the bicarbonate system has an effective cleaning range between pH's of about 8 and 10, with reduced cleaning properties outside these ranges.

EXAMPLE 4

OXIDATION-REDUCTION POTENTIAL AND CLEANING

Table 4 exemplifies the cleaning effect in relationship to oxidation-reduction potential (ORP). The data demonstrates the ability to remove proteinaceous soils, using a variety of ozone solutions with a pH greater than 7, when an ORP reading of greater than 750 milli-volts is obtained (lines 8–17). Conversely, much lower levels of cleaning are found below this ORP (lines 1–7), where soil removal value similar to the control air study (line 1) are obtained. These examples teach the application of using ORP readings to evaluate the cleaning potential of an ozonated solution.

EXAMPLE 5

RESIDENCE TIME AND CLEANING

Table 5 illustrates the effect of cleaning ability, of an ozonated solution, over distance and time; i.e., the effect of various residence times in the tubing before reaching the cleaning point. The increase in residence time was done by sequentially increasing the distance between the CIP holding tank containing the ozonated solution and the contact site where the ozonated solution is employed for cleaning. The data exemplifies the ability to pump ozonated cleaning solutions to remote locations, and with common residence times (60–120 seconds) found in typical CIP de-soiling operations, with no apparent degradation in the cleaning capacity of the system. The data illustrates the novel ability to stabilize, and utilize, alkaline ozone solutions for removing proteinaceous soils. These results establish the novelty of the invention in contrast to prior art disclosures which direct the skilled artisan away from alkaline cleaning compositions.

EXAMPLE 6

EFFECTS OF A LEWIS BASE ON CLEANING

Table 6 illustrates the effect of various Lewis base additives (under pH buffered conditions) on air and ozone cleaning of the proteinaceous soil. As with previous examples, the injection of air as a control study led to little or no cleaning (see Table 6, rows 1, 2, 5, 8, 11, 5, 19, 22, 25, 28). In contrast, when ozone is injected (rows 3–4, 6–7, 9–10, 12–14, 16–18, 20–21, 23–24, 26, 28–29) these bases, at levels as low as 50 ppm, can be quite effective at protein soil removal; even if the system is buffered to relatively low pH's (8.0 and 10.3) as compared to typical CIP cleaning. It is also shown that the soil elimination typically increases with increasing adjuvant level (cf., rows 6 and 7, 12 to 14, 23 and 24). Also, as before, an elevated pH leads to enhanced protein removal (cf., rows 3 and 4, 7 and 10, 14 and 18, 21 and 24, 26 and 28). One adjuvant that is especially noteworthy is the bicarbonate system (rows 5–10), where exceptional cleaning was even found at the low pH (8.0) level. Additionally, these additives give a greater, than mere additive, effect on cleaning. This nonobvious performance is demonstrated by the following examples: rows 3 (ozone alone) +5 (adjuvant alone) is less than row 7 (ozone+adjuvant), or rows 4+8 <row 10, or rows 4+15 <row 18, etc.

EXAMPLE 7

EFFECTS OF A SURFACTANT ON CLEANING

Table 7 illustrates the effect of various organic surfactants on ozone cleaning of the proteinaceous soil. The results demonstrate that common surfactants can be used with the ozone cleaning procedure without a negative detriment to soil removal and, actually, some give slight positive results to the elimination.

EXAMPLE 8

CLEANING CERAMIC-GLASS

Table 8 illustrates the effect of cleaning ability, of an ozonated solution, for removing proteinaceous soil from a ceramic-glass surface. The data demonstrates the ability to remove soil from hard surfaces other than stainless steel (liens 2 and 4), and also the lack of removal when ozone is not present (lines 1 and 3).

TABLE 1

THE EFFECT OF METAL HYDROXIDES AND OZONE ON PROTEIN REMOVAL FROM STAINLESS STEEL

| Conditions[1] | Gas | Spray Time (minutes) | Liquid Flow Rate (gal/min) | NaOH Conc. (ppm) | KOH Conc. (ppm) | pH | Delta L-value[2] | Delta Whiteness Index (WI)[3] | % Soil Removal[4] |
|---|---|---|---|---|---|---|---|---|---|
| A) non ozone studies | | | | | | | | | |
| 1  moderate acidity | air | 10 | 1.00 | — | — | 2.3[5] | 4.5 | −0.4 | 0.0% |
| 2  low acidity | air | 10 | 1.00 | — | — | 5.3[5] | 5.8 | 4.0 | 11.4% |
| 3  neutral | air | 10 | 1.00 | — | — | 7.0 | 6.1 | 3.2 | 9.1% |

TABLE 1-continued

THE EFFECT OF METAL HYDROXIDES AND OZONE ON PROTEIN REMOVAL FROM STAINLESS STEEL

| | Conditions[1] | Gas | Spray Time (minutes) | Liquid Flow Rate (gal/min) | NaOH Conc. (ppm) | KOH Conc. (ppm) | pH | Delta L-value[2] | Delta Whiteness Index (WI)[3] | % Soil Removal[4] |
|---|---|---|---|---|---|---|---|---|---|---|
| 4 | neutral | air | 10 | 0.50 | — | — | 7.4 | 0.06 | −0.5 | 0.0% |
| 5 | low alkaline | air | 10 | 0.50 | 25 | — | 8.7 | 0.2 | 1.5 | 4.3% |
| 6 | moderate alkaline | air | 10 | 0.50 | 250 | — | 10.8 | 1.2 | 5.3 | 15.1% |
| 7 | moderate alkaline | air | 10 | 0.50 | 500 | — | 11.3 | 0.7 | 3.9 | 11.1% |
| 8 | moderate alkaline | air | 10 | 1.00 | 500 | — | 12.2 | 5.5 | 3.7 | 10.6% |
| 9 | high alkaline | air | 20 | 0.21 | — | 1000 | 12.2 | 0.5 | 3.3 | 9.4% |
| 10 | high alkaline | air | 10 | 0.50 | 1000 | — | 12.3 | 1.5 | 5.3 | 15.1% |
| 11 | high alkaline | air | 10 | 1.00 | 1000 | — | 12.4 | 3.7 | 1.2 | 3.4% |
| 12 | high alkaline | air | 10 | 1.00 | 5000 | — | 13.2 | 3.5 | 4.3 | 12.3% |
| 13 | high alkaline | air | 10 | 1.00 | 10000 | — | 13.3 | 3.0 | 4.5 | 12.9% |
| B) ozone studies | | | | | | | | | | |
| 14 | moderate acidity | $O_3$ | 10 | 0.31 | — | — | 2.1[6] | 4.0 | 2.2 | 6.3% |
| 15 | moderate acidity | $O_3$ | 10 | 1.00 | — | — | 2.3[5] | 2.0 | −4.4 | 0.0% |
| 16 | low acidity | $O_3$ | 10 | 1.00 | — | — | 5.3[5] | 6.2 | 2.1 | 6.0% |
| 17 | neutral | $O_3$ | 10 | 1.00 | — | — | 7.0 | 4.3 | −2.8 | 0.0% |
| 18 | neutral | $O_3$ | 10 | 0.50 | — | — | 7.4 | −0.1 | −0.5 | 0.0% |
| 19 | low alkaline | $O_3$ | 10 | 0.50 | 25 | — | 8.7 | 3.9 | 11.3 | 32.3% |
| 20 | low alkaline | $O_3$ | 15 | 1.00 | 25 | — | 8.5 | 16.7 | 34.5 | 98.6% |
| 21 | low alkaline | $O_3$ | 10 | 0.50 | 50 | — | 9.3 | 3.7 | 11.0 | 31.4% |
| 22 | low alkaline | $O_3$ | 10 | 0.50 | 150 | — | 10.0 | 3.9 | 12.1 | 34.6% |
| 23 | moderate alkaline | $O_3$ | 10 | 0.50 | 250 | — | 10.8 | 4.2 | 16.7 | 47.7% |
| 24 | moderate alkaline | $O_3$ | 10 | 0.50 | 500 | — | 11.3 | 6.9 | 26.5 | 75.7% |
| 25 | high alkaline | $O_3$ | 20 | 0.08 | — | 1000 | 12.2 | 1.0 | 3.5 | 10.0% |
| 26 | high alkaline | $O_3$ | 20 | 0.21 | — | 1000 | 12.2 | 14.7 | 33.5 | 95.7% |
| 27 | high alkaline | $O_3$ | 20 | 0.99 | — | 1000 | 12.2 | 17.1 | 34.9 | 99.7% |
| 28 | high alkaline | $O_3$ | 10 | 0.50 | 1000 | — | 12.3 | 7.3 | 27.1 | 77.4% |
| 29 | high alkaline | $O_3$ | 10 | 0.50 | 1500 | — | 12.4 | 6.5 | 25.5 | 72.9% |
| 30 | high alkaline | $O_3$ | 10 | 1.00 | 5000 | — | 13.2 | 11.5 | 29.9 | 85.4% |
| 31 | high alkaline | $O_3$ | 10 | 1.00 | 10000 | — | 13.3 | 15.3 | 28.9 | 82.6% |

[1]Experimental: ozone was generated at a rate of: air flow = 40 SCFH, 15 psi, 6.3 amps, and injected into water at a temperature = 74° F., with a variable spray rate and reaction time.
[2]Delta L = ending L value of cleaned coupon minus starting L value of soiled coupon.
[3]Delta WI = ending WI value of cleaned coupon minus starting WI value of soiled coupon.
[4]% Soil Removal = 100 × [delta WI/(avg. cleaned WI − avg. soiled WI)] = 100 × [(delta WI)/(40 − 5)].
[5]pH adjusted with $H_2SO_4$.
[6]pH adjusted with $H_3PO_4$.

TABLE 2

THE EFFECT OF VARIOUS LEWIS BASES AND OZONE ON PROTEIN REMOVAL FROM STAINLESS STEEL

| | Conditions[1] | Gas | Reaction Time (minutes) | NaOH Conc. (ppm) | $Na_4SiO_4$ Conc. (ppm) | $Na_5P_3O_{10}$ Conc. (ppm) | $Na_2CO_3$ Conc. (ppm) | $NaHCO_3$ Conc. (ppm) | $Na_3BO_3$ Conc. (ppm) | pH | Delta L-value[2] | % Soil Removal[3] |
|---|---|---|---|---|---|---|---|---|---|---|---|---|
| 1 | sodium orthosilicate | $O_3$ | 10 | 0 | 250 | 0 | 0 | 0 | 0 | 9.4 | 11.9 | 86.6% |
| 2 | sodium orthosilicate | $O_3$ | 10 | 0 | 500 | 0 | 0 | 0 | 0 | 9.7 | 14.1 | 78.5% |
| 3 | sodium orthosilicate | $O_3$ | 10 | 0 | 1000 | 0 | 0 | 0 | 0 | 11.1 | 12.7 | 74.8% |
| 4 | sodium orthosilicate | $O_3$ | 10 | 0 | 5000 | 0 | 0 | 0 | 0 | 13.2 | 15.3 | 92.1% |
| 5 | sodium orthosilicate | $O_3$ | 10 | 0 | 10000 | 0 | 0 | 0 | 0 | 13.4 | 17.6 | 100.2% |
| 6 | sodium orthosilicate | air | 10 | 0 | 10000 | 0 | 0 | 0 | 0 | 13.5 | 0.6 | 4.7% |
| 7 | sodium tripolyphosphate | $O_3$ | 10 | 0 | 0 | 500 | 0 | 0 | 0 | 9.1 | 10.4 | 80.4% |
| 8 | sodium tripolyphosphate | $O_3$ | 10 | 0 | 0 | 1000 | 0 | 0 | 0 | 9.1 | 13.0 | 101.8%[4] |
| 9 | sodium tripolyphosphate | $O_3$ | 10 | 0 | 0 | 5000 | 0 | 0 | 0 | 9.2 | 12.9 | 101.5%[4] |
| 10 | sodium tripolyphosphate | $O_3$ | 10 | 0 | 0 | 10000 | 0 | 0 | 0 | 9.2 | 13.2 | 102.6%[4] |
| 11 | sodium tripolyphosphate | air | 10 | 0 | 0 | 10000 | 0 | 0 | 0 | 9.2 | 0.1 | 1.1% |
| 12 | sodium carbonate | $O_3$ | 10 | 0 | 0 | 0 | 500 | 0 | 0 | 10.2 | 11.6 | 94.1% |
| 13 | sodium carbonate | $O_3$ | 10 | 0 | 0 | 0 | 1000 | 0 | 0 | 10.3 | 9.8 | 80.0% |
| 14 | sodium carbonate | $O_3$ | 10 | 0 | 0 | 0 | 5000 | 0 | 0 | 10.8 | 10.4 | 84.3% |
| 15 | sodium carbonate | $O_3$ | 10 | 0 | 0 | 0 | 10000 | 0 | 0 | 11.0 | 12.2 | 98.4% |
| 16 | sodium carbonate | air | 10 | 0 | 0 | 0 | 10000 | 0 | 0 | 11.1 | 3.1 | 24.6% |
| 17 | sodium hydroxide | $O_3$ | 10 | 5000 | 0 | 0 | 0 | 0 | 0 | 13.2 | 11.5 | 85.6% |
| 18 | sodium hydroxide | $O_3$ | 10 | 10000 | 0 | 0 | 0 | 0 | 0 | 13.3 | 15.3 | 92.5% |
| 19 | sodium hydroxide | air | 10 | 10000 | 0 | 0 | 0 | 0 | 0 | 13.3 | 3.0 | 20.8% |
| 20 | sodium bicarbonate | $O_3$ | 30 | 0 | 0 | 0 | 0 | 25 | 0 | 7.7 | 4.3 | 34.4% |
| 21 | sodium bicarbonate | $O_3$ | 30 | 0 | 0 | 0 | 0 | 50 | 0 | 7.8 | 3.2 | 25.0% |
| 22 | sodium bicarbonate | $O_3$ | 30 | 0 | 0 | 0 | 0 | 100 | 0 | 8.2 | 10.3 | 80.3% |
| 23 | sodium bicarbonate | $O_3$ | 30 | 0 | 0 | 0 | 0 | 250 | 0 | 8.4 | 13.9 | 88.8% |
| 24 | sodium bicarbonate | $O_3$ | 30 | 0 | 0 | 0 | 0 | 1000 | 0 | 8.6 | 12.2 | 99.1% |

TABLE 2-continued

THE EFFECT OF VARIOUS LEWIS BASES AND OZONE ON PROTEIN REMOVAL FROM STAINLESS STEEL

| Conditions[1] | | Gas | Reaction Time (minutes) | NaOH Conc. (ppm) | $Na_4SiO_4$ Conc. (ppm) | $Na_5P_3O_{10}$ Conc. (ppm) | $Na_2CO_3$ Conc. (ppm) | $NaHCO_3$ Conc. (ppm) | $Na_3BO_3$ Conc. (ppm) | pH | Delta L-value[2] | % Soil Removal[3] |
|---|---|---|---|---|---|---|---|---|---|---|---|---|
| 25 | sodium bicarbonate | air | 30 | 0 | 0 | 0 | 0 | 1000 | 0 | 8.7 | 0.5 | 3.4% |
| 26 | sodium bicarbonate | $O_3$ | 30 | 0 | 0 | 0 | 0 | 1000 | 0 | 7.5 | 12.7 | 101.3% |
| 27 | sodium bicarbonate | $O_3$ | 30 | 0 | 0 | 0 | 0 | 2000 | 0 | 6.5 | 13.7 | 102.9% |
| 28 | sodium borate | $O_3$ | 30 | 0 | 0 | 0 | 0 | 0 | 1225 | 7.0[5] | 3.9 | 28.1% |
| 29 | sodium borate | $O_3$ | 30 | 0 | 0 | 0 | 0 | 0 | 1225 | 8.0[5] | 3.1 | 24.0% |
| 30 | sodium borate | $O_3$ | 30 | 0 | 0 | 0 | 0 | 0 | 1225 | 9.0[5] | 9.8 | 82.7% |
| 31 | sodium borate | $O_3$ | 30 | 0 | 0 | 0 | 0 | 0 | 1225 | 10.0[5] | 8.2 | 64.6% |

[1]Experimental: ozone was generated at a rate of: air flow = 40 SCFH, 15 psi, 6.3 amps, and injected into water at a temperature = 74° F., with a spray flow of 1.0 gal/min, and a reaction time of 10 minutes.
[2]Delta L = ending L value of cleaned coupon minus starting L value of soiled coupon.
[3]Delta WI = ending WI value of cleaned coupon minus starting WI value of soiled coupon.
[4]% Soil Removal = 100 × [delta WI/(avg. cleaned WI − avg. soiled WI)] = 100 × [(delta WI)/(40 − 5)]; greater than 100% — coupon became more reflective.
[5]pH adjusted with NaOH.

TABLE 3

THE EFFECT OF SODIUM BICARBONATE, ADDED FROM SOFTENED NATURAL MINERAL WATER AT VARIOUS pH's, AND OZONE ON PROTEIN REMOVAL FROM STAINLESS STEEL

| Conditions[1] | | | pH | Ozonated L-value | Soiled L-value | Delta L-value[2] | % Soil Removal[3] |
|---|---|---|---|---|---|---|---|
| 1 | run | 21 (244 ppm $NaHCO_3$)[4] | 7.8 | 65.08 | 63.79 | 1.28 | 10% |
| 2 | run | 2 (244 ppm $NaHCO_3$)[4] | 8.7 | 76.86 | 63.35 | 13.51 | 103%[5] |
| 3 | run | 9 (244 ppm $NaHCO_3$)[4] | 9.0 | 75.77 | 63.61 | 12.15 | 94% |
| 4 | run | 13 (244 ppm $NaHCO_3$)[4] | 9.5 | 76.98 | 63.05 | 13.93 | 104%[5] |
| 5 | run | 39 (244 ppm $NaHCO_3$)[4] | 10.0 | 77.31 | 63.86 | 13.45 | 106%[5] |
| 6 | run | 102 (244 ppm $NaHCO_3$)[4] | 12.2 | 65.97 | 63.72 | 2.25 | 18% |

[1]Experimental: ozone was generated at a rate of: air flow-40 SCFH, 15 psi, 6.3 amps., and injected into the softened mineral water (containing 244 ppm of $NaHCO_3$ from natural mineral sources), at a temp = 74° F., with a spray flow of 1.0 gal/min, and a reaction time of 30 minutes. NaOH was used to vary the pH.
[2]Delta L — ending L value of cleaned (ozonated) coupon minus starting L value of soiled coupon.
[3]% Soil Removal — 100 × [delta L/(avg. new-cleaned L − soiled L], where the avg. new-cleaned L is taken from an avg. of 100 new coupons, and is L = 76.5.
[4]Bicarbonate level from natural mineral water.
[5]Greater than 100% cleaning since the coupon became more reflective than a new, avg. cleaned coupon.

TABLE 4

THE EFFECT OF OXIDATION-REDUCTION POTENTIAL (ORP) AT pH's ABOVE 8.0 ON PROTEIN REMOVAL FROM STAINLESS STEEL

| Conditions[1] | | | Gas | ORP (mV) | Ozonated L-value | Soiled L-value | Delta L-value[2] | % Soil Removal[3] |
|---|---|---|---|---|---|---|---|---|
| 1 | run | 92 | air | 24 | 64.98 | 63.43 | 1.55 | 11.9% |
| 2 | run | 57 | $O_3$ | 219 | 58.05 | 57.28 | 0.77 | 4.0% |
| 3 | run | 58 | O3 | 274 | 58.96 | 57.97 | 0.99 | 5.3% |
| 4 | run | 11 | O3 | 554 | 65.30 | 64.22 | 1.08 | 8.8% |
| 5 | run | 59 | $O_3$ | 600 | 60.87 | 59.25 | 1.61 | 9.4% |
| 6 | run | 20 | $O_3$ | 703 | 65.08 | 63.79 | 1.28 | 10.1% |
| 7 | run | 60 | $O_3$ | 717 | 59.23 | 58.00 | 1.23 | 6.7% |
| 8 | run | 61 | $O_3$ | 777 | 62.67 | 57.77 | 4.90 | 26.1% |
| 9 | run | 57 | $O_3$ | 819 | 72.02 | 63.86 | 8.17 | 64.6% |
| 10 | run | 26 | $O_3$ | 850 | 74.75 | 60.81 | 13.93 | 88.8% |
| 11 | run | 39 | $O_3$ | 909 | 77.31 | 63.86 | 13.45 | 106.4%[4] |
| 12 | run | 97 | $O_3$ | 920 | 77.09 | 64.02 | 13.07 | 104.7%[4] |
| 13 | run | 13 | $O_3$ | 940 | 76.98 | 63.05 | 13.93 | 103.6%[4] |
| 14 | run | 15 | $O_3$ | 949 | 76.27 | 63.81 | 12.45 | 98.2% |
| 15 | run | 25 | $O_3$ | 965 | 76.50 | 63.66 | 12.84 | 100.0%[4] |
| 16 | run | 16 | $O_3$ | 980 | 76.73 | 64.10 | 12.62 | 101.9%[4] |
| 17 | run | 103 | $O_3$ | 999 | 76.85 | 64.02 | 14.07 | 102.5%[4] |

[1]Experimental: the variable ORP values were obtained using a variety of reaction conditions; such as variable amperage charges to the ozone generator, mixes of $NaOH$—$NaHBO_3$—$NaHCO_3$, run times, pH's, and gas flow rates. All reactions were done at a temp = 74° F., with a spray flow of 1.0 gal/min.

TABLE 4-continued

THE EFFECT OF OXIDATION-REDUCTION POTENTIAL (ORP) AT pH's ABOVE 8.0 ON PROTEIN REMOVAL FROM STAINLESS STEEL

| Conditions[1] | Gas | ORP (mV) | Ozonated L-value | Soiled L-value | Delta L-value[2] | % Soil Removal[3] |
|---|---|---|---|---|---|---|

[2]Delta L — ending L value of cleaned (ozonated) coupon minus starting L value of soiled coupon.
[3]% Soil Removal = 100 × [delta L/(avg. new-cleaned L − soiled L)], where the avg. new-cleaned L is taken from an avg. of 100 new coupons, and is L − 76.5.
[4]Greater than 100% cleaning since the coupon became more reflective than a new, avg. cleaned coupon.

TABLE 5

THE EFFECT OF RESIDENCE TIME ON PROTEIN REMOVAL FROM STAINLESS STEEL, USING AQUEOUS OZONE SOLUTIONS

| Conditions[1] | | Residence Time (seconds) | Ozonated L-value | Soiled L-value | Delta L-value[2] | % Soil Removal[3] |
|---|---|---|---|---|---|---|
| 1 | run | 8 | 31 | 76.11 | 63.38 | 12.72 | 97% |
| 2 | run | 19 | 92 | 76.76 | 62.45 | 14.30 | 102%[4] |
| 3 | run | 25 | 153 | 76.50 | 63.66 | 12.84 | 100% |
| 4 | run | 97 | 214 | 77.09 | 64.02 | 13.07 | 105%[4] |

[1]Experimental: ozone was generated at a rate of: air flow = 40 SCFH, 15 psi, 6.3 amps, and injected into water a temp = 74° F., with a solution pumping rate of 1 min/gal, at a pH = 8.9 with 1000 ppm NaHCO$_3$.
[2]Delta L — ending L value of cleaned (ozonated) coupon minus starting L value of soiled coupon.
[3]% Soil Removal = 100 × [delta L/(avg. new-cleaned L − soiled L)], where the avg. new-cleaned L is taken from an avg. of 100 new coupons, and is L − 76.5.
[4]Greater than 100% cleaning since the coupon became more reflective than a new, avg. cleaned coupon.

TABLE 6

THE EFFECT OF VARIOUS LEWIS BASES AND OZONE ON PROTEIN REMOVAL FROM STAINLESS STEEL

| | Conditions[1] | Gas | NaHCO$_3$ Conc. (ppm) | Na$_5$P$_3$O$_{10}$ Conc. (ppm) | Na$_2$HPO$_4$ Conc. (ppm) | Na$_4$SiO$_4$ Conc. (ppm) | pH | Delta L-value[2] | Delta Whiteness Index (WI)[3] | % Soil Removal[4] |
|---|---|---|---|---|---|---|---|---|---|---|
| 1 | control (no additive) | air | 0 | 0 | 0 | 0 | 8.0 | 0.3 | 0.5 | 1.4% |
| 2 | control (no additive) | air | 0 | 0 | 0 | 0 | 10.3 | −0.5 | 0.5 | 1.4% |
| 3 | control (no additive) | O$_3$ | 0 | 0 | 0 | 0 | 8.0 | 4.5 | 4.4 | 12.6% |
| 4 | control (no additive) | O$_3$ | 0 | 0 | 0 | 0 | 10.3 | 6.9 | 19.8 | 56.6% |
| 5 | bicarbonate system | air | 1000 | 0 | 0 | 0 | 8.0 | 1.8 | 7.8 | 22.2% |
| 6 | bicarbonate system | O$_3$ | 250 | 0 | 0 | 0 | 8.0 | 11.6 | 16.2 | 46.3% |
| 7 | bicarbonate system | O$_3$ | 1000 | 0 | 0 | 0 | 8.0 | 14.99 | 29.3 | 83.7% |
| 8 | bicarbonate system | air | 1000 | 0 | 0 | 0 | 10.3 | 1.5 | −3.9 | 0.0% |
| 9 | bicarbonate system | O$_3$ | 250 | 0 | 0 | 0 | 10.3 | 15.8 | 33.4 | 95.4% |
| 10 | bicarbonate system | O$_3$ | 1000 | 0 | 0 | 0 | 10.3 | 14.9 | 34.4 | 98.3% |
| 11 | tripolyphosphate system | air | 0 | 1000 | 0 | 0 | 8.0 | −0.2 | −1.0 | 0.0% |
| 12 | tripolyphosphate system | O$_3$ | 0 | 50 | 0 | 0 | 8.0 | 4.3 | 1.8 | 5.1% |
| 13 | tripolyphosphate system | O$_3$ | 0 | 250 | 0 | 0 | 8.0 | 2.8 | 3.2 | 9.1% |
| 14 | tripolyphosphate system | O$_3$ | 0 | 1000 | 0 | 0 | 8.0 | 2.9 | 6.2 | 17.7% |
| 15 | tripolyphosphate system | air | 0 | 1000 | 0 | 0 | 10.3 | 0.9 | 0.3 | 1.0% |
| 16 | tripolyphosphate system | O$_3$ | 0 | 50 | 0 | 0 | 10.3 | 8.7 | 21.0 | 60.0% |
| 17 | tripolyphosphate system | O$_3$ | 0 | 250 | 0 | 0 | 10.3 | 8.8 | 23.7 | 67.7% |
| 18 | tripolyphosphate system | O$_3$ | 0 | 1000 | 0 | 0 | 10.3 | 11.4 | 37.1 | 100.0% |
| 19 | orthophosphate system | air | 0 | 0 | 1000 | 0 | 8.0 | 1.5 | −6.5 | 0.0% |
| 20 | orthophosphate system | O$_3$ | 0 | 0 | 250 | 0 | 8.0 | 5.2 | 2.6 | 7.4% |
| 21 | orthophosphate system | O$_3$ | 0 | 0 | 1000 | 0 | 8.0 | 2.4 | 1.4 | 4.0% |
| 22 | orthophosphate system | air | 0 | 0 | 1000 | 0 | 10.3 | 0.1 | 1.8 | 5.1% |
| 23 | orthophosphate system | O$_3$ | 0 | 0 | 250 | 0 | 10.3 | 11.0 | 15.3 | 43.7% |
| 24 | orthophosphate system | O$_3$ | 0 | 0 | 1000 | 0 | 10.3 | 10.2 | 18.1 | 51.7% |
| 25 | orthosilicate system | air | 0 | 0 | 0 | 1000 | 8.0 | 0.9 | 4.5 | 12.8% |
| 26 | orthosilicate system | O$_3$ | 0 | 0 | 0 | 250 | 8.0 | 5.0 | 2.3 | 6.6% |
| 27 | orthosilicate system | air | 0 | 0 | 0 | 1000 | 10.3 | 0.2 | −1.2 | 0.0% |
| 28 | orthosilicate system | O$_3$ | 0 | 0 | 0 | 250 | 10.3 | 11.3 | 23.2 | 66.3% |
| 29 | orthosilicate system | O$_3$ | 0 | 0 | 0 | 1000 | 10.3 | 10.8 | 17.2 | 49.1% |

[1]Experimental: ozone was generated at a rate of: air flow = 40 SCFH, 15 psi, 6.3 amps, and injected into water at a temperature = 74° F., with a spray flow of 0.5 gal/min, and a reaction time of 10 minutes. The solutions wee buffered to the desired pH's using a boric acid;/sodium hydroxide buffer.
[2]Delta L = ending L value of cleaned coupon minus starting L value of soiled coupon.
[3]Delta WI = ending WI value of cleaned coupon minus starting WI value of soiled coupon.
[4]% Soil Removal = 100 × [delta WI/(avg. cleaned WI − avg. soiled WI)]

TABLE 7

THE EFFECT OF SURFACE ACTIVE AGENTS WITH OZONE ON PROTEIN REMOVAL FROM STAINLESS STEEL

| Conditions[1] | Gas | Surfactant Conc. (ppm) | Delta L-Value[2] | Delta Whiteness Index (WI)[3] | % Soil Removal[4] |
|---|---|---|---|---|---|
| 1 control (no additive) | air | 0 | 0.8 | −1.9 | 0.0% |
| 2 control (no additive) | $O_3$ | 0 | 10.9 | 25.2 | 72.1% |
| 3 Hostapur SAS 93[5] | $O_3$ | 50 | 13.8 | 27.9 | 79.7% |
| 4 Supra 2[6] | $O_3$ | 50 | 12.9 | 28.9 | 82.6% |
| 5 APG-325[7] | $O_3$ | 50 | 15.3 | 25.1 | 71.7% |

[1]Experimental: ozone was generated at a rate of: air flow = 40 SCFH, 15 psi, 6.3 amps, and injected into water at a temperature = 74° F., with a spray flow of 0.5 gal/min, and a reaction time of 10 minutes. The solutions wee buffered to the desired pH's using a boric acid;/sodium hydroxide buffer.
[2]Delta L = ending L value of cleaned coupon minus starting L value of soiled coupon.
[3]Delta WI = ending WI value of cleaned coupon minus starting WI value of soiled coupon.
[4]% Soil Removal = 100 × [delta WI/(avg. cleaned WI − avg. soiled WI)]
[5]A secondary alkane sulfonate (Hostapur SAS 93) − 93%, added at 50 ppm active.
[6]A cocoa dimethyl amine oxide − 32%, added at 50 ppm active.
[7]APG 325 is an alkyl glycoside − 40%, added at 50 ppm active.

TABLE 8

THE EFFECT OF AQUEOUS OZONE ON PROTEIN REMOVAL FROM CERAMIC GLASS

| Conditions[1] | Gas | Reaction Minutes | % Soil Removal[2] |
|---|---|---|---|
| 1 1000 ppm KOH | air | 2 | <10% |
| 2 1000 ppm KOH | $O_3$ | 2 | >90% |
| 3 1000 ppm KOH | air | 10 | <10% |
| 4 1000 ppm KOH | $O_3$ | 10 | about 100% |

[1]Experimental: ozone was generated at a rate of: air flow = 40 SCFH, 15 psi, 6.3 amps, and injected into water at a temperature = 74° F., with a spray flow of 1.0 ga./min.
[2]% Soil Removal is based on a visual inspection after straining with Coomassie Blue dye, and is a comparison of the cleaned vs. newly soiled cup stains.

Examples of Ozone Quenching and Sanitizing

EXAMPLE 9

FIG. 1 demonstrates the principle of using oxidation-reduction potential (ORP) as a measure of the ozone content for various aqueous-ozone cleaning systems. It was typical in the current experiments, and literature, to find an ORP~200 mV for systems of ~0 ppm ozone, with an exponential increase in ORP above ~700 mV. The data of FIG. 1 is illustrative for demonstrating the peracid quench effect.

Figure 2:
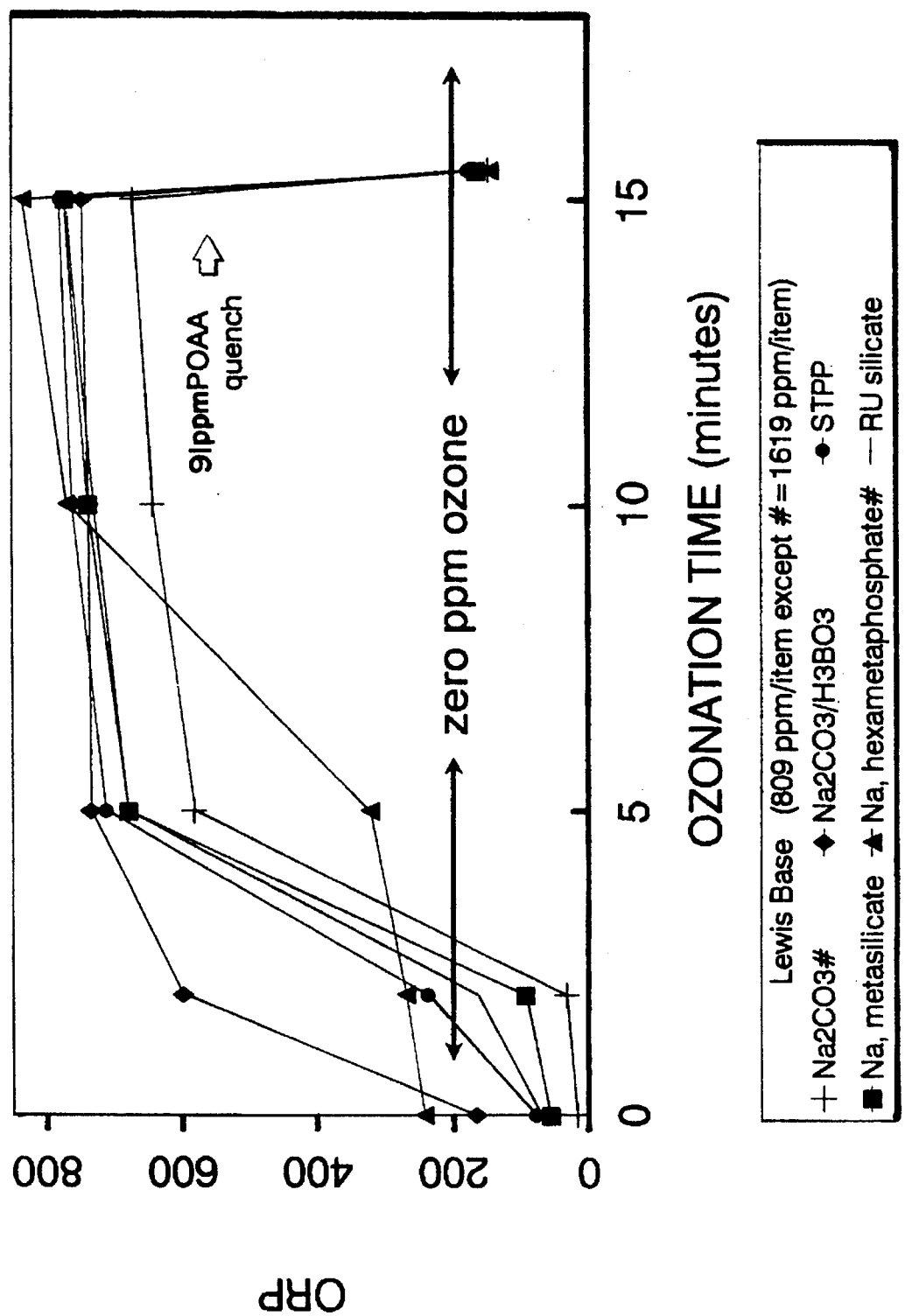

Table 9 illustrates the effective biocidal activity of various peracid compositions under typical use concentrations that are simultaneously effective for ozone quenching; i.e., usually between 25 and 200 ppm total peracid. The data demonstrates the effective reductions in microbial activity (>2-log), while FIGS. 2 and 3, and Table 10, illustrate the rapid quench of ozone in the ozone-cleaning systems upon the addition of the peracid sanitizer; i.e., the ORP of the ozonated cleaner go from ~200 mV at the start of the ozone cleaning process, to ~>700 mV at the end, to <200 mV (~0 ppm ozone) within 30 seconds after the peracid sanitizing composition is added (sanitizer added at t=15 or 30 min. and ozone reduction recorded 30 seconds later). The data shows that within a variety of Lewis base cleaning compositions (FIG. 2), peracid concentrations (cf., FIG. 2 and 3, Table 10), and surfactant or mixed peracid ozone-cleaning/sanitizing systems (Table 10) that a rapid, and effective, quench of the ozone is accomplished by the peracid sanitizing composition.

FIG. 4 illustrates the ozone quenching effect of using common peroxygen bleaches—hydrogen peroxide and sodium percarbonate—on ozone-cleaning systems. The data demonstrates the effectiveness of these adjuvents to likewise destroy ozone; however, it is known that the tested concentrations of peroxygen bleaches will not render significant microbial control. The data is significant since it is most common to prepare, in-situ, and employ the aforementioned peracid sanitizers with hydrogen peroxide. Consequently this allows for the hydrogen peroxide, usually present in large excess vs. the peracid, to rapidly catalyze and destroy the ozone-cleaner without significant loss in the peracid; thus allowing for simultaneous sanitizing and quenching.

TABLE 9

PERACID BIOCIDAL REDUCTION OF MICROBIALS

| Experiment[1] | Antimicrobial Peracids(s) Concentration(s) (ppm) | Microbe | Treatment Time (minutes) | Log Reduction vs. controls |
|---|---|---|---|---|
| 1. Control 1[2] | none (0 ppm) | Staph aureus | none | 0 |
| 2. Test 1[2] | POAA[3] (128 ppm) | Staph aureus | 0.5 | >5.0 |
| 3. Ex. 6a[4] | POAA[3] (50 ppm) | E. Coli | 0.5 | 3.5 |
| 4. Ex. 4a[4] | POFA[3] (50 ppm) | E. Coli | 0.5 | >7.3 |
| 5. Ex. 2c[4] | POAA/POFA[3] (25/25 ppm) | E. Coli | 0.5 | 7.0 |
| 6. Ex. 2a[4] | POAA/POFA[3] (50/50 ppm) | E. Coli | 0.5 | >7.3 |
| 7. Table II[4] | POAA/POOA[3] (25/5 ppm) | E. Coli | 0.5 | 3.8 |
| 8. Table II[4] | POPA/POOA[3] (25/6 ppm) | E. Coli | 0.5 | 3.9 |
| 9. Control 3[5] | none (0 ppm) | TPC[6] | none | 0 |
| 10. [5] | POAA[3] (30 ppm) | TPC[6] | pulsed | 2.4 |
| 11. [5] | POAA/POOA[3] (27/3 ppm) | TPC[6] | continuous | 2.4 |
| 12. Control 4[7] | none (0 ppm) | TPC[6] | none | 0 |
| 13. Ex. 1[7] | POAA[3] (48 ppm) | TPC[6] | 60 | 5.9 |
| 14. Ex. 3[7] | POPA[3] (48 ppm) | TPC[6] | 60 | 5.9 |
| 15. Ex. 4[7] | POBA[3] (48 ppm) | TPC[6] | 60 | 5.9 |

TABLE 9-continued

PERACID BIOCIDAL REDUCTION OF MICROBIALS

| Experiment[1] | Antimicrobial Peracids(s) Concentration(s) (ppm) | Microbe | Treatment Time (minutes) | Log Reduction vs. controls |
|---|---|---|---|---|
| 16. Ex. 6[7] | POGUA[3] (48 ppm) | TPC[6] | 60 | 4.4 |
| 17. Ex. 7[7] | POGYA[3] (48 ppm) | TPC[6] | 60 | 4.2 |
| 18. Ex. 8[7] | POLA[3] (48 ppm) | TPC[6] | 60 | 4.7 |
| 19. Ex. 9[7] | POCA[3] (48 ppm) | TPC[6] | 60 | 5.1 |

[1] Experimental: microbial reductions done under a variety of soiling conditions, where log reductions >2 deemed effective for demonstrating biocidal activity.
[2] Microbial reduction in unsoiled system.
[3] POAA = peroxyacetic acid, POFA = peroxyfatty acid mix of percaprylic and percapric acids, POOA = peroxyoctanoic, POPA = peroxypropionic acid, POBA = peroxybutyric acid, POGUA = peroxyglutaric acid, POGYA = peroxyglycolic acid, POLA = peroxylactic acid, POCA = peroxycitric acid.
[4] U.S. Pat. No. 5,200,189.
[5] U.S. Pat. No. 5,4090,713.
[6] TPC = total plate count
[7] Microbial reduction in soil loaded system.

EXAMPLE 10

The following experiment compares various quenching agents for ozone off-gas from aqueous solutions by chemical injection prior to spraying.

| Chemical = 1%H2O2 | | | |
|---|---|---|---|
| Pumping setting | calculate [H2O2] | Chamber Sump ORP | Gaseous [ozone] in spray chamber |
| 0.00 cc/min | 0.0 ppm | 840 mV | 6.5 ppm |
| 0.72 | 1.9 | 118 | 1.3 |
| 2.6 | 6.8 | 118 | 0.05 |

| -continued |
|---|
| Chemical = 1%NH4OH |
| Injection at 7 ppm level has only small quenching effect, which may be accounted for by pH increase. |
| Chemical = 1%NaHSO3 |
| Minimal reduction of gaseous ozone |
| Chemical = 1%Na2SO3 |
| Ozone gas monitor showed an increase, possibly due to interference effect |

The data demonstrates the effectiveness of the peroxide to simultaneously lower the liquid-phase ozone concentration, as measured by the drop in ORP, and the gas-phase ozone concentration, as measured by a commercial UV ozone monitor. Conversely, other additives, including typical stoichiometric reducing agents, had little effect on gaseous ozone removal.

TABLE 10

QUENCHING OF OZONE CLEANING SYSTEMS WITH PEROXYGEN SANITIZERS

| Ozone Cleaning Conditions[1] | Sanitizing-Quench Agents/ Levels (ppm) | Oxidation-Reduction Potential (ORP) Ozonation Cleaning Time[2] (minutes) | | |
|---|---|---|---|---|
| | | initial (0 min.) | final (30 min.) | quenched (30.5 min.) |
| 1. alkyl glycoside[3] | POAA[5]/(45 ppm) | 133 | 773 | 118 |
| 2. secondary alkane sulfonate[3] | POAA[5]/(45 ppm) | 115 | 819 | 160 |
| 3. alkyl diphenyl oxide sulfonate[3] | POAA[5]/(45 ppm) | 121 | 777 | 174 |
| 4. dialkyl sulfosuccinate/ mineral oil[4] | POAA[5]/(59 ppm) | 132 | 826 | 143 |
| 5. alcohol 8-ethoxylate[4] | POAA[5]/(91 ppm) | 160 | 715 | 170 |
| 6. alkyl sorbitan ethoxylate[4] | POAA[5]/(91 ppm) | 94 | 758 | 140 |
| 7. alkyl dimethyl amine oxide[4] | POAA[5]/(91 ppm) | 170 | 848 | 280 |
| 8. alkyl sulfate[4] | POAA[5], POOA[6], $H_2O_2$/(34,3, 119 ppm) | 169 | 832 | 165 |
| 9. alcohol 3-ethoxylate[4] | POAA[5], POOA[6], $H_2O_2$/(34,3, 119 ppm) | 120 | 779 | 122 |
| 10. alkyl dimethyl amine oxide[4] | POAA[5], POOA[6], $H_2O_2$/(34,3, 119 ppm) | 319 | 821 | 159 |

[1] Experimental: ozone was generated at a rate of: air flow = 40 SCFH, 15 psi, 6.3 amps, and injected into water at a temp = 74 F.
[2] The initial ORP time is before ozone injection, final time records ORP value at end of cleaning cycle, and quench ORP value is 30 seconds after final time.
[3] 24 ppm surfactant + 811 ppm ea. NaOH, H3BO3.
[4] 358 ppm surfactant + 811 ppm ea. NaOH, H3BO3.
[5] POAA = peroxyacetic acid.
[6] POOA = peroxyoctanoic acid.

We claim:

1. A method of cleaning and sanitizing solid surfaces comprising
   (a) contacting a soil or film residue on a solid surface with an ozonized cleaning aqueous composition having a pH of at least about 8 and comprising an effective concentration of an active ozone composition sufficient to produce an oxidation-reduction potential of at least about +550 mV with respect to an Ag/Agcl reference electrode;
   (b) treating the contacted solid surface with an aqueous sanitizing composition comprising an effective amount of a hydrogen peroxide, $C_1$–$C_{10}$ peroxyaliphatic carboxylic acid or a mixture thereof sufficient to reduce the oxidation-reduction potential below about +400 mV.

2. The method of claim 1, wherein the cleaning composition comprises 100 to 10,000 parts of sodium carbonate or bicarbonate, per each million parts by weight of the composition, and an effective concentration of active ozone providing an oxidation-reduction potential of at least +750 mV, prepared by injecting ozone into an aqueous alkaline solution having a pH between 7.5 and 10.

3. The method of claim 2, wherein the cleaning composition further comprises a sequestrant composition.

4. The method of claim 2, wherein the cleaning composition further comprises an effective wetting amount of a surfactant.

5. The method of claim 1, wherein the aqueous sanitizing composition comprises at least about 10 parts per million (ppm) of a $C_1$–$C_{10}$ peroxyaliphatic carboxylic acid.

6. The method of claim 5, wherein said peroxyaliphatic carboxylic acid comprises peroxyacetic acid, peroxyglutaric acid, peroxyoctanoic acid or mixtures thereof.

7. The method of claim 6, wherein said peroxyaliphatic carboxylic acid comprises peracetic acid.

8. The method of claim 5, wherein the aqueous sanitizing composition further comprises at least about 10 ppm of a free $C_1$–$C_{10}$ aliphatic carboxylic acid or a mixture thereof.

9. The method of claim 8, wherein said aliphatic carboxylic acid comprises acetic acid, glutaric acid, octanoic acid or mixtures thereof.

10. The method of claim 5, wherein the aqueous sanitizing composition comprises at least about 1 ppm of hydrogen peroxide.

11. The method of claim 5, wherein the aqueous sanitizing composition comprises:
    (a) about 10 to 150 ppm of a $C_1$–$C_{10}$ peroxyaliphatic carboxylic acid;
    (b) about 0 to 25 ppm of octanoic acid, and
    (c) about 2 to 200 ppm of hydrogen peroxide.

12. The method of claim 11, wherein said peroxyaliphatic carboxylic acid is peracetic acid.

13. A method of cleaning and sanitizing substantially fixed in-place process facilities comprising the steps of:
    (a) circulating an ozonized cleaning aqueous composition having a pH of at least 8 and comprising an effective concentration of an active ozone composition sufficient to produce an oxidation-reduction potential of at least about +550 mV with respect to an Ag/Agcl reference electrode;
    (b) circulating an aqueous sanitizing composition comprising an effective amount of hydrogen peroxide, a $C_1$–$C_{10}$ peroxyaliphatic carboxylic acid or a mixture thereof sufficient to reduce the oxidation-reduction potential below about +400 mV.

14. The method of claim 13, wherein the cleaning composition comprises 100 to 10,000 parts of sodium carbonate or bicarbonate, per each million parts by weight of the composition, and an effective concentration of active ozone providing an oxidation-reduction potential of at least +750 mV, prepared by injecting ozone into an aqueous alkaline solution having a pH between 8 and 10.

15. The method of claim 14, wherein the cleaning composition further comprises a sequestrant composition.

16. The method of claim 14, wherein the cleaning composition further comprises an effective wetting amount of a surfactant.

17. The method of claim 13, wherein the aqueous sanitizing composition comprises at least about 10 parts per million (ppm) of a $C_1$–$C_{10}$ peroxyaliphatic carboxylic acid or a mixture thereof.

18. The method of claim 14, wherein said peroxyaliphatic carboxylic acid comprises peroxyacetic acid, peroxyglutaric acid, peroxyoctanoic acid or mixtures thereof.

19. The method of claim 18, wherein said peroxyaliphatic carboxylic acid comprises peracetic acid.

20. The method of claim 17, wherein the aqueous sanitizing composition further comprises at least about 10 ppm of a free $C_1$–$C_{10}$ aliphatic carboxylic acid or a mixture thereof.

21. The method of claim 20, wherein said aliphatic carboxylic acid comprises acetic acid, glutaric acid, octanoic acid or mixtures thereof.

22. The method of claim 17, wherein the aqueous sanitizing composition comprises at least about 1 ppm of hydrogen peroxide.

23. The method of claim 17, wherein the aqueous sanitizing composition comprises:
    (a) about 10 to 150 ppm of a $C_1$–$C_{10}$ peroxyaliphatic carboxylic acid;
    (b) about 0 to 25 ppm of octanoic acid, and
    (c) about 2 to 200 ppm of hydrogen peroxide.

24. The method of claim 23, wherein said peroxyaliphatic carboxylic acid is peracetic acid.

25. The method of claim 13, wherein the process facilities comprise a milk line dairy.

26. The method of claim 13, wherein the process facilities comprise a continuous brewing system.

27. The method of claim 13, wherein the process facilities comprises a pumpable food system or beverage processing line.

* * * * *

UNITED STATES PATENT AND TRADEMARK OFFICE
CERTIFICATE OF CORRECTION

PATENT NO. : 5,567,444

DATED : October 22, 1996

INVENTOR(S) : Hei et al.

It is certified that error appears in the above-identified patent and that said Letters Patent is hereby corrected as shown below:

```
     Title page, item [63], please delete "20," and substitute
therefore --30,--
```

Signed and Sealed this

Twenty-second Day of July, 1997

*Attest:*

BRUCE LEHMAN

*Attesting Officer*    *Commissioner of Patents and Trademarks*